(12) United States Patent
Davidsen et al.

(10) Patent No.: US 7,749,520 B2
(45) Date of Patent: Jul. 6, 2010

(54) COMPOSITIONS AND METHODS FOR STABILIZING LIPID BASED ADJUVANT FORMULATIONS USING GLYCOLIPIDS

(75) Inventors: Jesper Davidsen, Solroed Strand (DK); Peter Andersen, Broenshoej (DK); Ida Rosenkrands, Vaerloese (DK)

(73) Assignee: Statens Serum Institut (DK)

( * ) Notice: Subject to any disclaimer, the term of this patent is extended or adjusted under 35 U.S.C. 154(b) by 1119 days.

(21) Appl. No.: 11/174,955

(22) Filed: Jul. 5, 2005

(65) Prior Publication Data

US 2006/0008519 A1 Jan. 12, 2006

Related U.S. Application Data

(60) Provisional application No. 60/585,908, filed on Jul. 7, 2004.

(30) Foreign Application Priority Data

Jul. 7, 2004 (DK) .............................. 2004 01070

(51) Int. Cl.
*A61K 45/00* (2006.01)
*A61K 51/00* (2006.01)
*A61K 47/44* (2006.01)

(52) U.S. Cl. .............. 424/278.1; 424/1.21; 424/283.1; 424/450

(58) Field of Classification Search ............... 424/1.21, 424/278.1, 283.1, 450
See application file for complete search history.

(56) References Cited

U.S. PATENT DOCUMENTS

| | | | |
|---|---|---|---|
| 4,235,871 A | 11/1980 | Papahadjopoulos et al. | |
| 4,975,282 A | 12/1990 | Cullis et al. | |
| 5,008,050 A | 4/1991 | Cullis et al. | |
| 5,026,546 A | 6/1991 | Hilgers | |
| 5,922,350 A | 7/1999 | Janoff et al. | |
| 6,806,355 B2 | 10/2004 | Joergensen | |
| 6,921,808 B2 | 7/2005 | Joergensen | |
| 2004/0057963 A1 | 3/2004 | Andersen et al. | |

FOREIGN PATENT DOCUMENTS

| | | |
|---|---|---|
| GB | 2 147 263 A | 5/1985 |
| WO | WO 96/10392 A1 | 4/1996 |
| WO | WO 02/30959 A2 | 4/2002 |

OTHER PUBLICATIONS

Holten-Andersen et al (Infection and Immunity, 72(3):1608-1617, 2004).*

Woodard et al, Comparison of Muramyl Depeptide, Trehalose Dimycolate, and Dimethyl Dioctadecyl Ammonium Bromide as Adjuvants in *Brucella abortus* 45/20 Vaccines, Infection and Immunity, pp. 409-412, vol. 30, No. 2, (Nov. 1980).

Van Rooij, Protective Antiviral Immune Responses to Pseudorabies Virus Induced by DNA Vaccination Using Dimethyldioctadecylammonium Bromide as an Adjuvant, Journal of Virology, pp. 10540-10545, vol. 76, No. 20, (Oct. 2002).

Szoka, Jr., et al, Procedure for Preparation of Liposomes with Large Internal Aqueous Space and High Capture by Reverse-Phase Evaporation Proc. Natl. Acad. Sci. USA, vol. 75, No. 9, pp. 4194-4198, (Sep. 1978).

Spargo et al, Cord Factor (a,a-trehalose 6,6'-dimycolate) Inhibits Fusion Between Phospholipid Vesicles, Proc. Natl. Acad. Sci. USA, vol. 88, pp. 737-740, (Feb. 1991).

Lindblad et al, Adjuvant Modulation of Immune Responses to Tyberculosis Subunit Vaccines, Infection and Immunity, vol. 65, No. 2, (Feb. 1997).

Harboe et al, B-Cell Epitopes and Quantification of the ESAT-6 Protein of Mycobacterium Tuberculosis, Infection and immunity, pp. 717-723, vol. 66, No. 2 (Feb. 1998).

Flynn et al, An Essential Role for Interferon Y in Resistance to Mycobacterium Tuberculosis Infection, pp. 2249-2254, vol. 178, (Dec. 1993).

Eriksson et al, Cholera Toxin and Its B Subunit Promote Dendritic Cell Vaccination with Different Influences on Th1 and Th2 Development, Infection and Immunity, vol. 71, No. 4, pp. 1740-1747, (Apr. 2003).

Cooper et al, Disseminated Tuberculosis in Interferon Y Gene-Disruptee Mice, J. Exp. Med. vol. 178, pp. 2243-2247, (Dec. 1993).

Collins & Kaufmann, The Many Faces of Host Responses to Tuberculosis, Immunology, 103, pp. 1-9, (Feb. 2001).

Brandt et al, ESAT-6 Subunit Vaccination Against Mycobacterium Tuberculosis, vol. 68, No. 2, Infection and Immunity, pp. 791-795, (Feb. 2000).

Wang et al, Enhanced Immunogenicity of BCG Vaccine by Using a Viral-Based GM-CSF Transgene Adjuvant Formulation, Vaccine 20, pp. 2887-2898 (Jul. 6, 2002).

Stanfield et al, Single-Dose Antenatal Tetanus Immunisation, The Lancet, pp. 215-219, (Feb. 3, 1973).

Uri Pick, Liposomes with a Large Trapping Capacity Prepared by Freezing and Thawing of Sonicated Phospholipid Mixtures, Archives of Biochemistry and Biophysics, vol. 212, No. 1, pp. 186-194, (Nov. 1981).

Ribeiro et al, Prepearation and characterization of Large Dioctadecyldimethylamonium Chloride Liposomes and Comparison with Small Sonicated Vesicles, Biochimica et Biophysica Acta, 733, pp. 172-179, (Aug. 24, 1983).

(Continued)

*Primary Examiner*—Rodney P. Swartz
(74) *Attorney, Agent, or Firm*—Howson & Howson LLP

(57) ABSTRACT

The present invention relates to liposome formulations that are physically stable. In particular the present invention relates to steric stabilization of cationic liposomes by incorporating glycolipids into the liposomes. The stabilized liposomes can be used either as an adjuvant for antigenic components or as a drug delivery system. In particular the invention relates to vaccines with adjuvants in aqueous media for immunization, where the final product is stable.

17 Claims, 11 Drawing Sheets

OTHER PUBLICATIONS

Papahadjopoulos et al, Phospholipid Model Membranes II. Permeability Properties of Hydrated Liquid Crystals, Biochim biophys Acta,135, (4), pp. 639-652, (Sep. 9, 1967).

Li et al, Lyophilization of Cationic Lipid-Protamine-DNA (LPD) Complexes, Journal of Pharmaceutical Sciences, vol. 89, No. 3, pp. 355-364, (Mar. 2000).

Hilgers et al, DDA as a Immunological Adjuvant, 143(5):pp. 494-503, Discussion 574-6, (Jun. 1992).

Gregoriadis et al, Vaccine Entrapment in Liposomes, Methods, vol. 19, Issue 1, pp. 156-162, (Sep. 1999).

Dzata et al, Immunopotentiation of Cattle Vaccinated with a Soluble *Brucella abortus* Antigen with Low LPS Content: an Analysis of Cellular and Huoral Immune Responses, Veterinary Microbiology, 29, pp. 15-26, (Sep. 1991).

Crowe et al, Interaction of Cord Factor (Alpha, Alpha'-Trehalose-6,6'-Dimycolate) with Phospholipids, Biochim Biophys Acta, 1194(1):53-60, (Aug. 24, 1994).

Ben-Yehuda et al, Immunogenicity and Safety of a Novel IL-2-Supplemented Liposomal Influenza Vaccine (INFLUSOME-VAC) in Nursing-Home Residents, Vaccine, 21, pp. 3169-3178, (Jul. 4, 2003).

Carmona-Ribeiro et al, Salt-Induced Aggregation and Fusion of Dioctadecyldimethylammonium Chloride and Sodium Dihexadecylphosphate Vesicles, Biophys J. 50(4):621-8, (Oct. 1983).

Holten-Anderson et al, Combination of the Cationic Surfactant Dimetyly Diocrtadecyl Ammonium Bromide and Synthetic Mycobacterial Cord Factor as an Efficient Adjuvant for Tuberculosis Subunit Vaccines, Infection and Immunity, vol. 72, No. 3, pp. 1608-1617, (Mar. 2004).

Olsen et al, Protection of Mice with a Tuberculosis Subunit Vaccine Based on a Fusion Protein of Antigen 85B and ESAT-6, Infection and immunity, vol. 69, No. 5, pp. 2772-2778, (May 2001).

Kirby et al, Dehydration-Rehydration Vesicles: A Simple Method for High Yield Drug Entrapment in Liposomes, Biotechnology, pp. 979-984, (Nov. 1984).

\* cited by examiner

\* The formulations aggregated and could not be measured by PCS

COMPOSITIONS AND METHODS FOR STABILIZING LIPID BASED ADJUVANT FORMULATIONS USING GLYCOLIPIDS

CROSS-REFERENCE TO RELATED APPLICATIONS

This is an application claiming the benefit under 35 USC 119(e) of U.S. Provisional Patent Application No. 60/585,908, filed Jul. 7, 2004 and priority under 35 USC 119 of Danish Patent application No. 2004 01070, filed Jul. 7, 2004, which are incorporated by reference.

BACKGROUND OF THE INVENTION

The present invention relates to liposome formulations that are physically stable. In particular the present invention relates to steric stabilization of cationic liposomes by an unique film method whereby glycolipids are incorporated into the liposomes. The stabilized liposomes can be used either as an adjuvant for antigenic components or as a drug delivery system. In particular the invention relates to vaccines with adjuvants in aqueous media for immunization, where the final product is stable.

The first vaccines used in humans to produce immunity against infectious diseases consisted of live, attenuated pathogens. The attenuated forms were either naturally occurring closely related organisms or obtained through serial passages in culture. One example is tuberculosis that is combated by vaccination with attenuated but living strains of *Mycobacterium bovis* (BCG vaccine). However, the efficacy of this procedure does not always provide satisfactory resistance to human tuberculosis in every population. There is therefore a need for new and efficient ways of producing immunity against tuberculosis and other infectious diseases. A particular promising approach has been to isolate and use recombinant forms of immunodominant antigens such as the early secretory antigenic target (ESAT-6) and antigen 85 (Ag85) as a vaccine. These vaccines are well-defined and side-reactions are minimized.

Unfortunately, many highly purified substances, e.g. purified recombinant proteins, are not very immunogenic and do not produce an effective immune response protective against the real infectious disease. This fact is well known and many attempts have been made to increase the immunogenic properties by combining the substance in question with so-called adjuvants. Depending on the pathogen, protection may require that either a humoral or a cell-mediated response predominate. The development of a specific kind of immune response (humoral or cell-mediated) can be determined by the choice of adjuvant.

Protective immunity against an intracellular pathogen like *M. tuberculosis* requires a cell-mediated immune response, and a suitable adjuvant for a subunit vaccine directed against TB should enhance a Th1 response (Lindblad et al, 1997). It is generally believed that antibodies do not play an important role in immunity to TB whereas cell-mediated release of IFN-gamma (interferon gamma) is the most important cytokine involved in protection (Collins & Kaufmann, 2001).

A large number of adjuvants that induce a cell mediated immune response have been suggested but in general without any being ideal in all respects.

One particular effective type of adjuvant that promotes a cell-mediated immune response is quaternary ammonium compounds, such as dimethyldioctadecylammonium (DDA) (Hilgers and Snippe, 1992). DDA is a synthetic amphiphile comprising a hydrophilic positively charged dimethylammonium head-group and two long hydrophobic alkyl chains. In an aqueous environment DDA self-assemble to form vesicular bilayers similar to liposomes made from natural phospholipids. Combinations of DDA and other immunomodulating agents have been described. Administration of Arquad 2HT, which comprises DDA, in humans was promising and did not induce apparent side effects (Stanfield et al., 1973).

An experimental vaccine based on culture filtrate proteins from *M. tuberculosis* and DDA generated a protective immune response against TB in mice (Andersen, 1994). Vaccination of mice with a fusion protein of *M. tuberculosis* proteins ESAT-6 and Ag85B, and DDA/MPL as adjuvant, provides protection similar to that obtained by BCG vaccination (Olsen et al, 2001). These studies demonstrate that, in contrast to e.g. alum, DDA-based adjuvants are able to induce a protective immune response against TB in mice. Moreover, DDA has been used as an adjuvant for a DNA vaccine against pseudorabies virus leading to enhanced T-cell responses and anti-viral immunity (van Rooij et al, 2002).

Addition of TDM (alpha,alpha'-trehalose 6,6'-dimycolate) oil emulsions to DDA solutions was investigated by Woodard et al (1980) as adjuvants for *Brucella abortus* vaccines based on heat killed bacteria. Neither DDA alone nor the mixtures of DDA and TDM was able to induce protection. In another study of a *Brucella abortus* subunit vaccine based on a soluble protein extract, a combination of DDA and TDM was also used as adjuvant (Dzata et al, 1991), and the mixture was found to enhance the immune responses (antibody levels, skin test response, and IL-2 levels) observed compared to DDA alone. Holten-Andersen et al (2004) studied a combination of DDA liposomes and a suspension of TDB (alpha,alpha'-trehalose 6,6'-dibehenate), and administration of the ESAT-6 antigen with this adjuvant mixture was found to induce a strong protective immune response against tuberculosis which was significantly higher than when ESAT-6 was administered in DDA liposomes.

Unfortunately, suspensions of amphiphilic quaternary ammonium compounds such as DDA alone or mixtures of DDA and MPL, TDM or TDB as described above are physically unstable and prolonged storage at 4° C. is not possible without the occurrence of aggregation and precipitates. As precipitation will prevent clinical use of the formulation, the lack of stability of DDA formulations has so far been a major obstacle for any application in humans.

In Great Britain Pat. No. 2147263-A, Takahashi and Tsujii describes stabilization of vesicles from quaternary ammonium compounds by mixing two quaternary ammonium compounds together or adding various detergents to the quaternary ammonium compound.

In U.S. Pat. No. 5,026,546, Hilgers and Weststrate describes stabilization of an adjuvant suspension of DDA with a polymer of acrylic acid crosslinked with polyallyl sucrose.

Lyophilization of cationic lipid-protamin-DNA complexes for transfection of cells was described by Li et al (2000). The effect of adding traditional cryoprotectants like monosaccharides and disaccharides was evaluated, and disaccharides were found to preserve particle size better than monosaccharides. Also non-lyophilized lipid-protamin-DNA complexes stabilised with 10% sucrose maintained a stable particle size after 8 weeks storage at 4° C., but the transfection efficiency was higher in lyophilized than in non-lyophilized samples.

U.S. Pat. No. 5,922,350 describes a method for extending storage of liposomes e.g. based on phospholipids by adding sugars like trehalose and sucrose before the dehydration of the liposomes. Furthermore, the patent describes that delayed loading of the preformed, stored liposomes is feasible by a combination of concentration gradients and the dehydration-rehydration process.

Liposomes of phospholipids for drug delivery (fusogenic liposomes) stabilized with a polyethylene glycol derivative are described in WO 96/10392. Another drug delivery formulation described in WO 02/03959 discloses a formulation comprising cationic liposomes and neutral liposomes where each liposome group either carries the same or different therapeutic agents.

Preferred methods for making liposome preparations are described by Bangham (Bangham et al., 1965). This preparation involves dissolving phospholipids in an organic solvent which is then evaporated to dryness leaving a thin lipid film on the inside of the test tube. The dry lipid film is then hydrated in an appropriate amount of aqueous phase and the mixture is heated to above the phase transition temperature of the lipids and allowed to "swell". The resulting liposomes which consist of multilamellar vesicles (MLV's) are dispersed by shaking the test tube. The lipids constituting the vesicular bilayer membranes are organized such that the hydrophobic hydrocarbon "tails" are oriented toward the center of the bilayer while the hydrophilic "heads" orient towards the in- and outside aqueous phase, respectively. This preparation provides the basis for producing unilamellar vesicles (UV) by methods such as sonication (Papahadjopoulos et al., 1967) or extrusion as described by Cullis et al. in U.S. Pat. No. 5,008,050.

Other techniques used to prepare vesicles are reverse-phase evaporation introduced by Szoka and Papahadjopoulos (Szoka and Papahadjopoulos, 1978; U.S. Pat. No. 4,235,871). This technique consists of forming a water-in-oil emulsion of lipids in an organic solvent and an aqueous buffer solution containing a substance to be encapsulated. Removal of the organic solvent under reduced pressure produces a viscous gel. When this gel collapses an aqueous suspension of lipid vesicles are formed.

Another method described by Carmona-Ribeiro and Chaimovich (Carmona-Ribeiro and Chaimovich, 1983) involves injecting an organic e.g. chloroform, methanol, ethanol, solution of the desired lipids into an aqueous buffer where the lipids spontaneously forms liposomes as the solvent evaporates.

The liposomes can also be prepared by the aqueous heat method as described for DDA by Holten-Andersen et al (2004) by which a suspension of the liposome forming compound in aqueous buffer is heated to e.g. 80° C. by intermittent shaking for 20 minutes followed by cooling to room temperature.

Above mentioned "aqueous heat method", used and described by Woodard et al (1980), Dzata et al (1991) and Holten-Andersen et al (2004) does not stabilize solutions of DDA and TDB.

In one particular preferred method protein antigens are entrapped within preformed vesicles by the dehydration-rehydration method (Kirby and Gregoriadis, 1984) in which an oligonucleotide, peptide or protein present in the aqueous phase is entrapped by freeze drying followed by rehydration of the lyophilized liposomes.

Alternatively the antigen is incorporated using the freeze and thaw technique described by Pick (Pick, 1981) and by Bally et al. in U.S. Pat. No. 4,975,282. In this technique vesicles are mixed with the protein antigen and repeatedly snap frozen in liquid nitrogen and warmed to temperatures above the main phase transition temperature of the relevant lipids. The vesicles may be further processed to remove any non-entrapped antigen e.g. by washing and centrifuging.

It has been shown that acylated glycosides such as TDB and cord factor isolated from the mycobacterial cell wall, TDM, inhibits fusion between phospholipid vesicles (Spargo et al., 1991 and Crowe et al. 1994). The hydrophilic trehalose moiety is likely to be immobilized at the surface of the vesicles, thus increasing the hydration force that is an important primary barrier to fusion. Alternatively the immobilized trehalose moiety might act as a steric barrier to fusion (Spargo et al., 1991).

Liposomes from phospholipids (without TDB) are presently used experimentally as adjuvants in e.g. influenza vaccine (Ben-Yehuda et al., 2003). Another example is IMUXEN™ liposomal vaccine against influenza (Lipoxen Technologies Ltd.; Gregoriadis et al., 1999).

As quaternary ammonium compounds and especially DDA is a very promising candidate for an effective vaccine adjuvant but has the major disadvantage of being physically un-stable in aqueous solution forming aggregates and precipitates during storage it is much needed to stabilise the vesicles formed. The present invention describes a new method of stabilizing adjuvant formulations composed of cationic lipids such as DDA. Additionally, by this method the adjuvant effect of the formulation is enhanced.

SUMMARY OF THE INVENTION

The present invention discloses compositions and methods for stabilizing cationic liposome suspensions by incorporating glycolipids e.g. acylated glycosides such as alpha,alpha'-trehalose 6,6'-dibehenate (TDB) or alpha,alpha'-trehalose 6,6'-dimycolate (TDM) into liposomal bilayers made from amphiphilic quaternary ammonium compounds such as DDA, DODA, DOTAP, DODAP or DOTMA. The strongly hydrated sugar head-groups of the glycolipids increases the overall hydration of the liposomal bilayers, which prevents dehydration of the quaternary ammonium head-groups and aggregation caused by reduced charge repulsion of the cationic vesicles. This stabilization of DDA is not obtained alone by adding the sugar e.g. trehalose or sucrose or by a simple mixing of the quaternary ammonium compounds and glycolipids. The present invention also discloses the use of these stabilized liposomes as vaccine adjuvants.

DETAILED DESCRIPTION OF THE DRAWINGS

Figure 1A:
FIG. 1A shows the structure of dimethyldioctadecylammonium (DDA-X).
Figure 1B:
FIG. 1B shows the structure of dimethyldioctadecenylammonium (DODA-X).
Figure 1C:
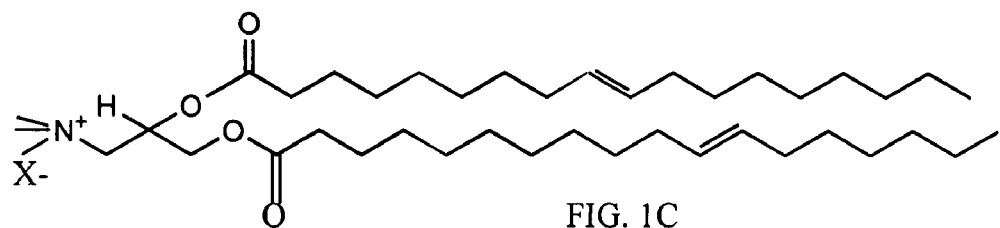
FIG. 1C shows the structure of 1,2-dioleolyl-3-trimethylammonium propane (DOTAP-X).
Figure 1D:
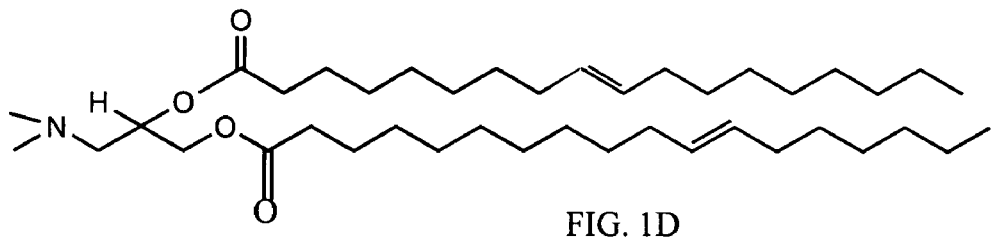
FIG. 1D shows the structure of 1,2-dioleoyl-3-dimethylammonium propane (DODAP).
Figure 1E:
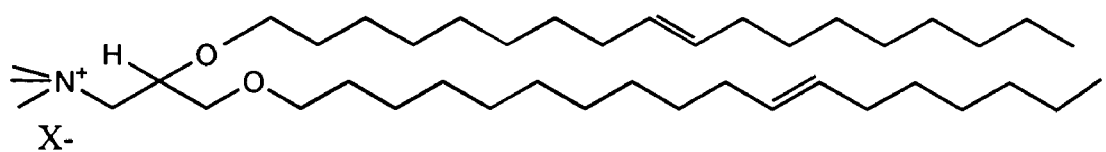
FIG. 1E shows the structure of N-[1-1-(2,3-dioleyloxy) propyl-N,N,N-trimethylammonium (DOTMA).
Figure 2:
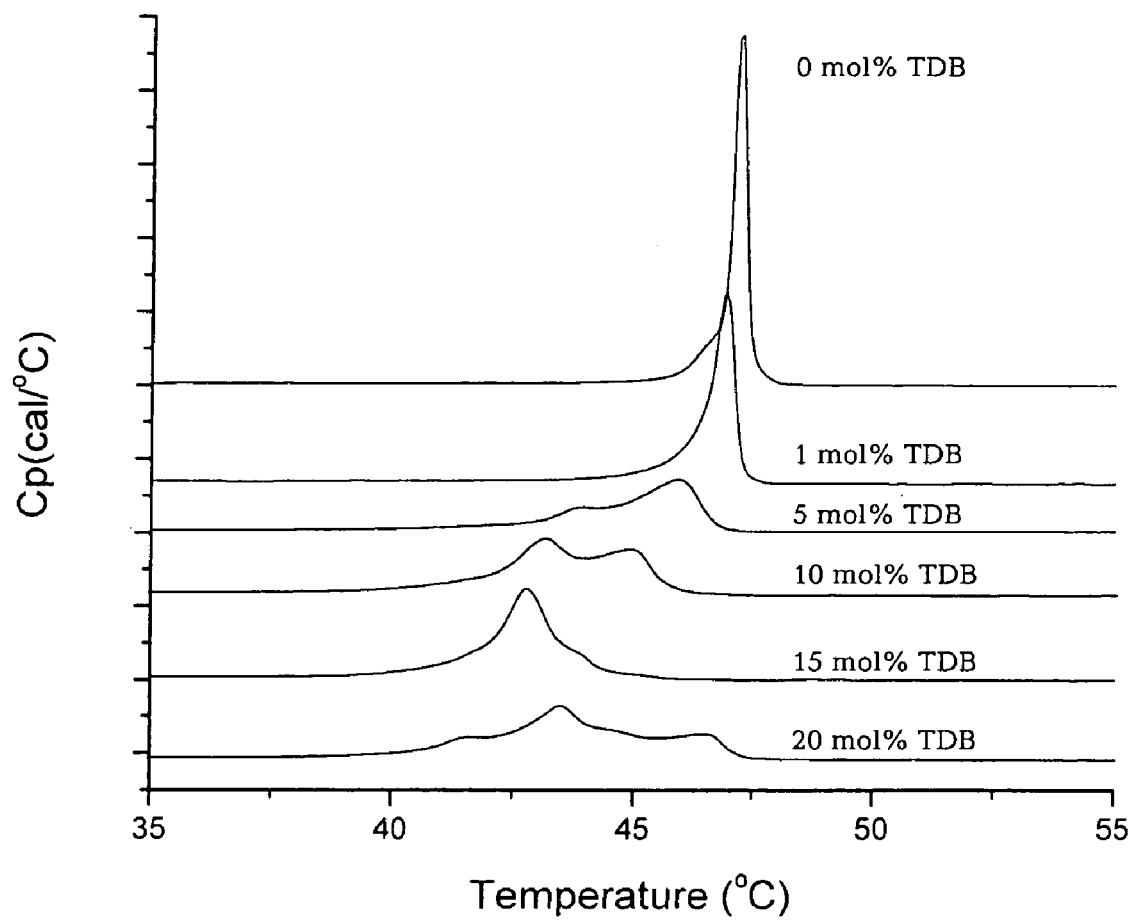

FIG. 2 is a graph of DSC thermograms of multilamellar liposomes composed of DDA-B with increasing concentrations of TDB (from top to bottom), obtained at a scan rate of 30 C/h. The liposomes were dispersed in 10 mM Tris buffer with pH 7.4. The thermograms clearly illustrate that TDB is inserted in the DDA liposome membranes.

Figure 3:
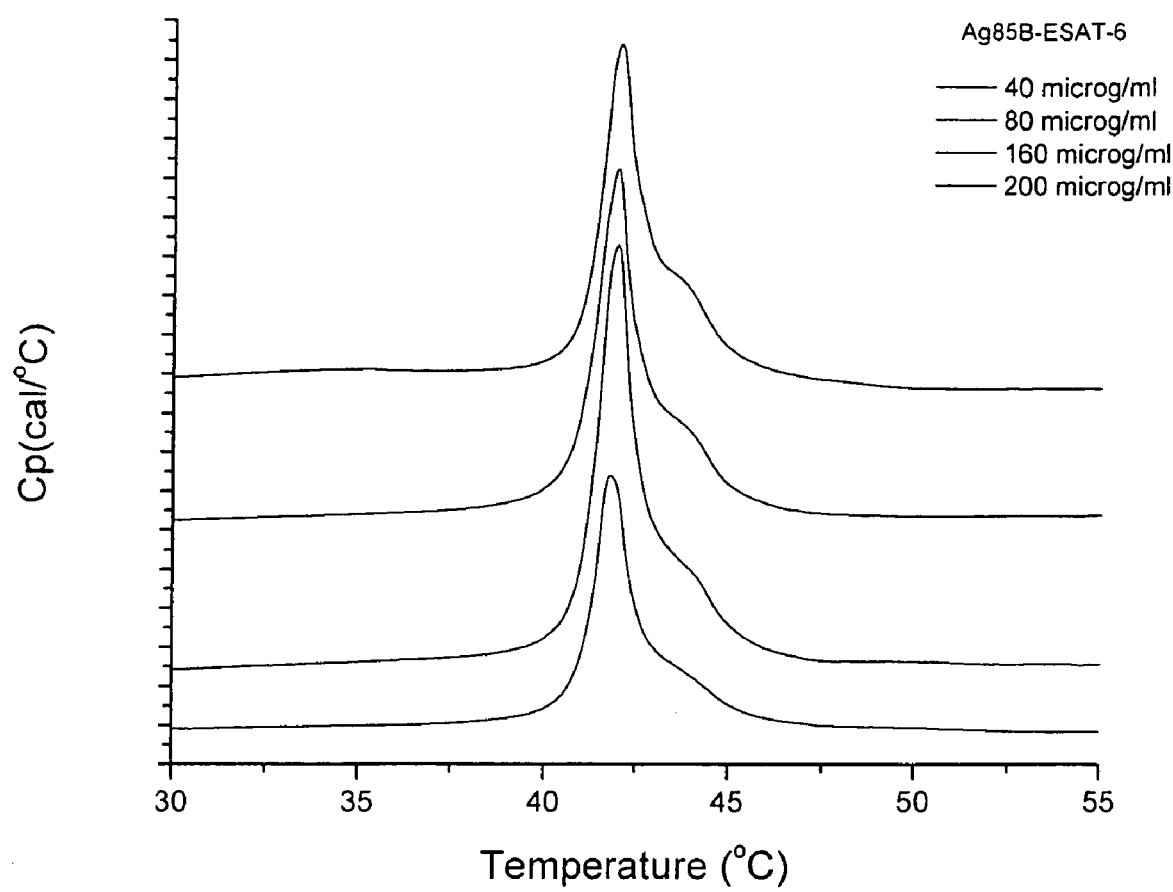

FIG. 3 is a graph of DSC thermograms of multilamellar liposomes composed of DDA-B and TDB with increasing concentrations the antigen Ag85B-ESAT-6 (from top to bottom), obtained at a scan rate of 30 C/h. The liposomes were dispersed in 10 mM Tris buffer with pH 7.4. The thermograms clearly illustrate that the phase transition temperature does not change by incorporating an antigen into the liposomes.

Figure 4:
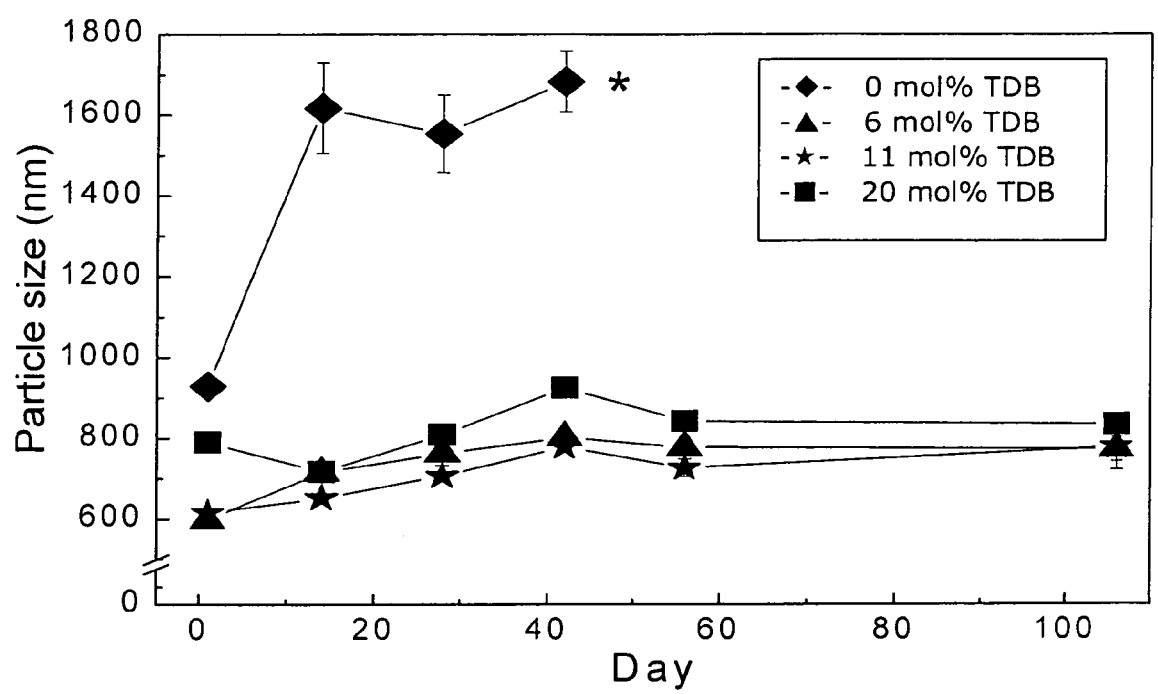

FIG. 4 is a graph showing the time development of average particle size of DDA liposomes containing 0 mol % (-♦-), 6 mol % (-▲-), 11 mol % (-*-) and 20 mol % (-■-) TDB. The liposomes were dispersed in 10 mM Tris buffer adjusted to pH 7.4. A significant increase is observed for DDA liposomes without TDB after 14 days.

Figure 5:
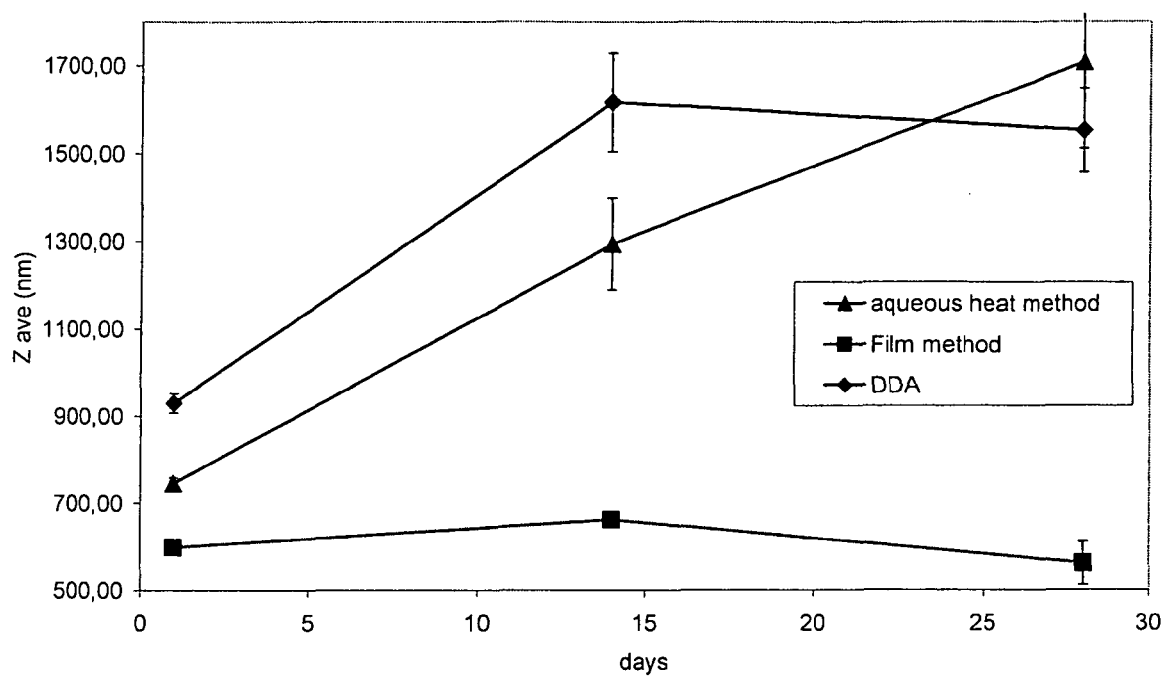

FIG. 5 is a line graph showing the time development of average particle size of DDA liposomes (-♦-) and DDA liposomes containing 11 mol % TDB prepared by the aqueous heat method (-▲-), 11 mol % TDB prepared by the film method (-■-). The liposomes were dispersed in 10 mM Tris buffer adjusted to pH 7.4. A significant increase was observed for DDA liposomes and for DDA/TDB liposomes prepared by the aqueous heat method after 14 days.

Figure 6:
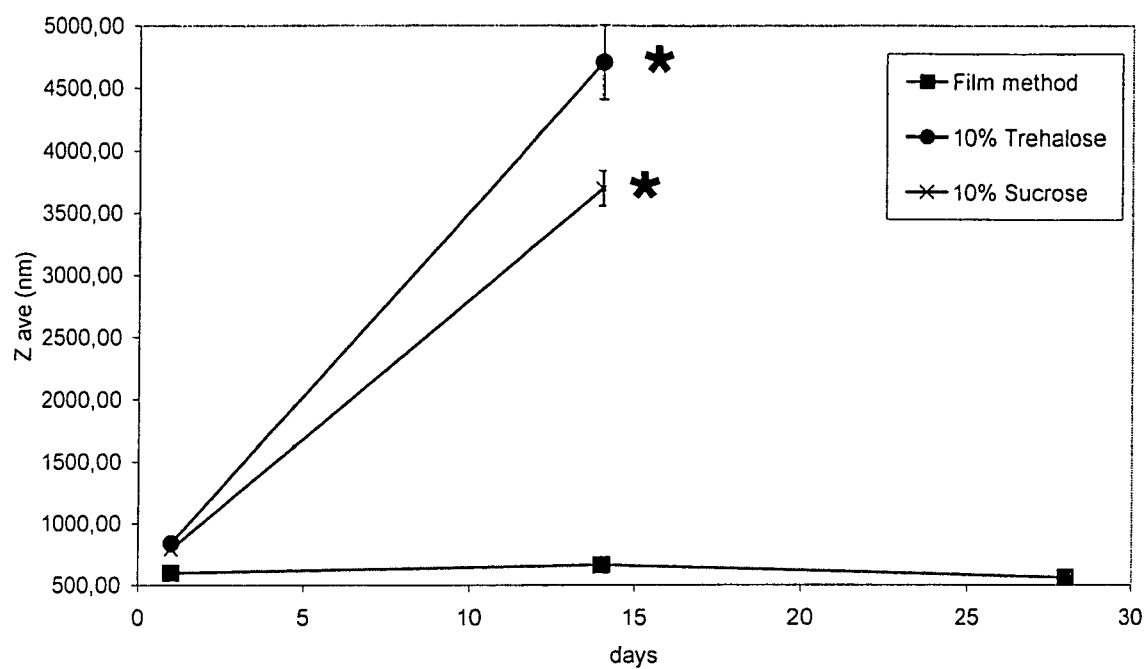

FIG. 6 is a line graph showing the time development of average particle size of DDA liposomes containing 11 mol % TDB (-■-), 10% (w/v) trehalose (-●-) and 10% (w/v) sucrose (-X-). The liposomes were dispersed in 10 mM Tris buffer adjusted to pH 7.4. DDA liposomes containing trehalose and sucrose aggregated to a degree rendering it impossible to make further measurements by PCS after 14 days.

Figure 7A:
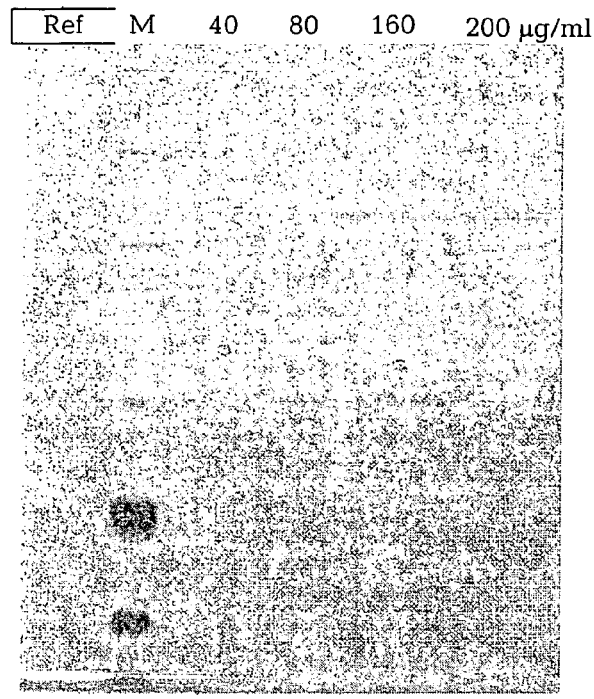
Figure 7B:
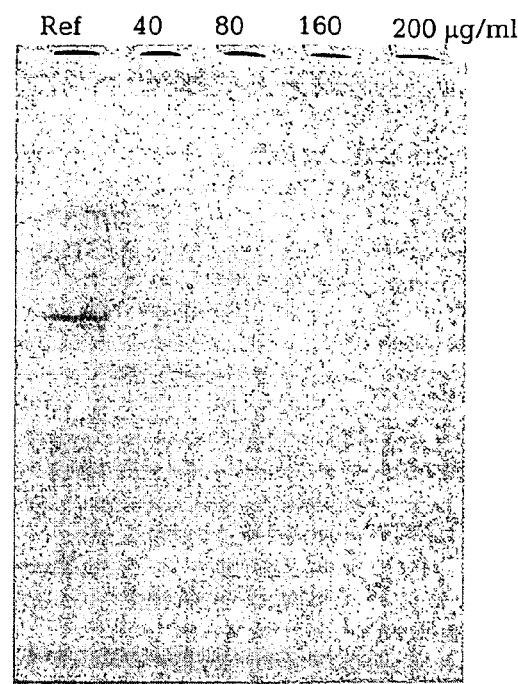

FIGS. 7A and 7B show the results of SDS-PAGE analysis of supernatant and resuspended pellet of ultracentrifuged Ag85B-ESAT-6 of final ready-to-use vaccines performed to visualize antigen adsorption to the cationic liposomes.

Figure 8:
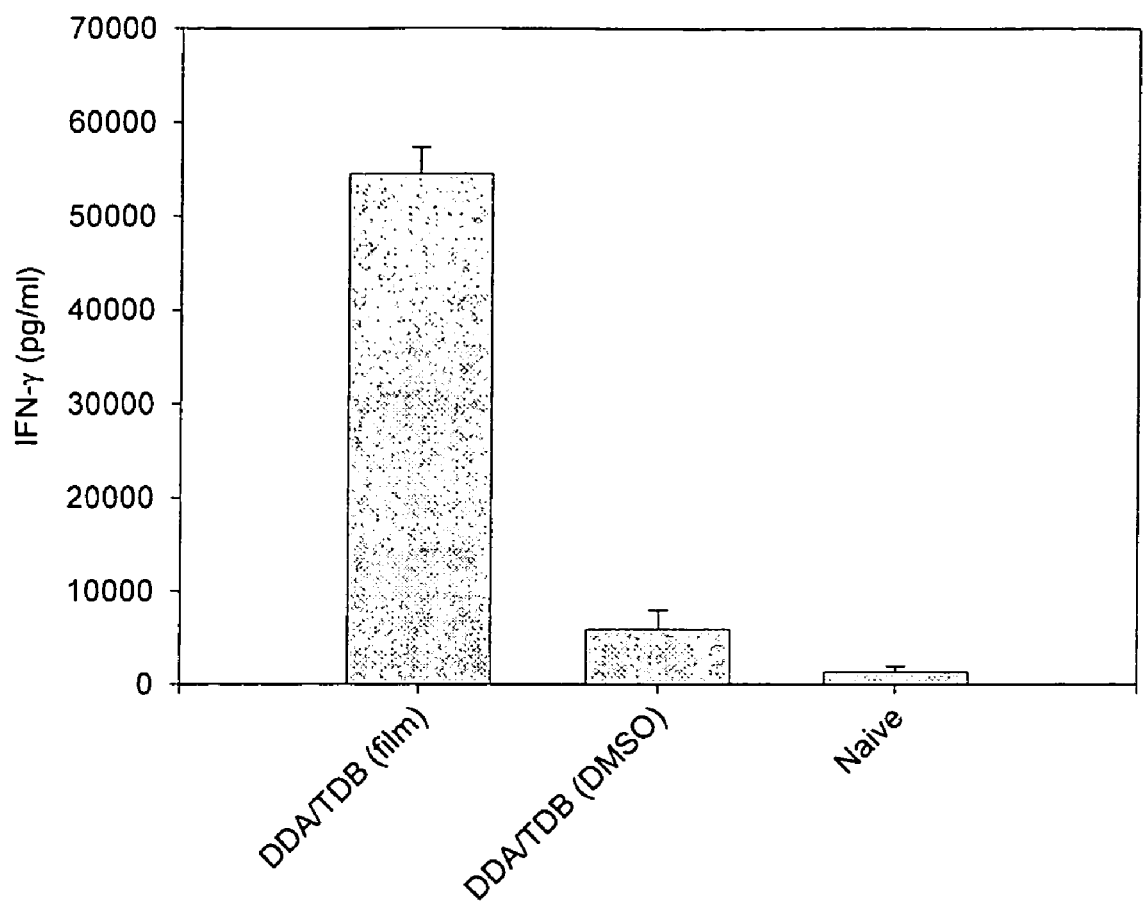

FIG. 8 is a bar chart showing the release of IFN-gamma from blood lymphocytes isolated from C57Bl/6j mice immunized with Ag85B-ESAT-6/DDA/TDB prepared as described in example 1 of this invention or Ag85B-ESAT-6/DDA/TDB prepared as described by Holten-Andersen et al (2004). Lymphocytes were isolated 1 week after the third immunization, and stimulated with Ag85B-ESAT-6 at 5 μg/ml.

Figure 9A:
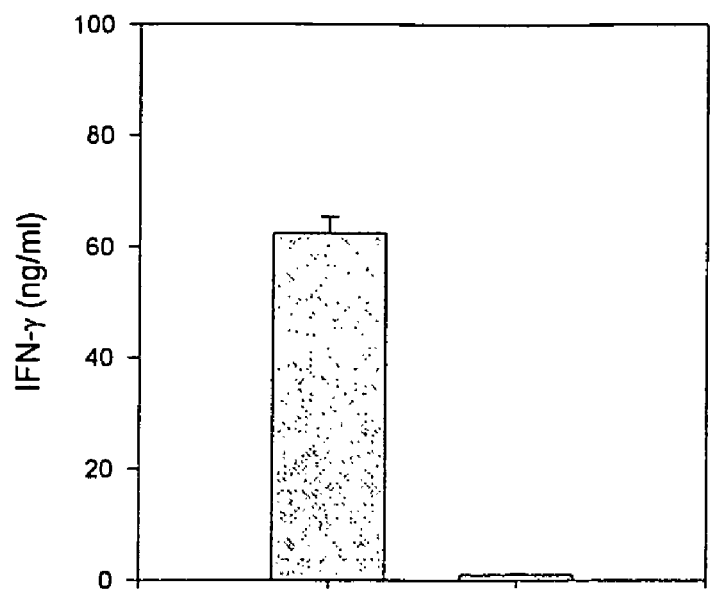

FIG. 9A is a bar chart showing the release of IFN-gamma from blood lymphocytes isolated from C57Bl/6j mice immunized with 2 μg of Ag85B-ESAT-6/DDA/TDB or Ag85B-ESAT-6 in 500 μg Alum. Blood lymphocytes were isolated 1 week after the third immunization and restimulated in vitro with 5 μg/ml of Ag85B-ESAT-6.

Figure 9B:
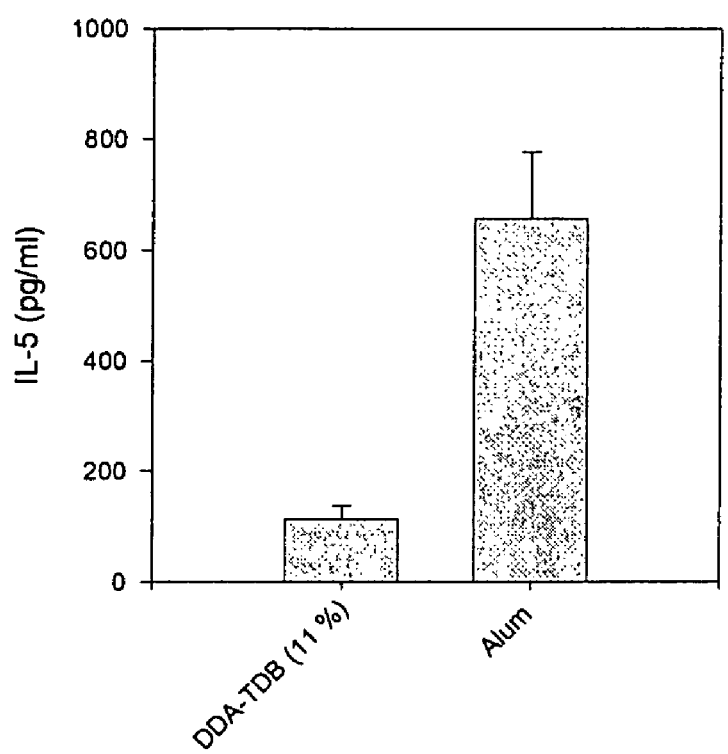

FIG. 9B is a bar chart showing the release of IL-5 from blood lymphocytes isolated from C57Bl/6j mice immunized with 2 μg of Ag85B-ESAT-6/DDA/TDB or Ag85B-ESAT-6 in 500 υg Alum.

Figure 10A:
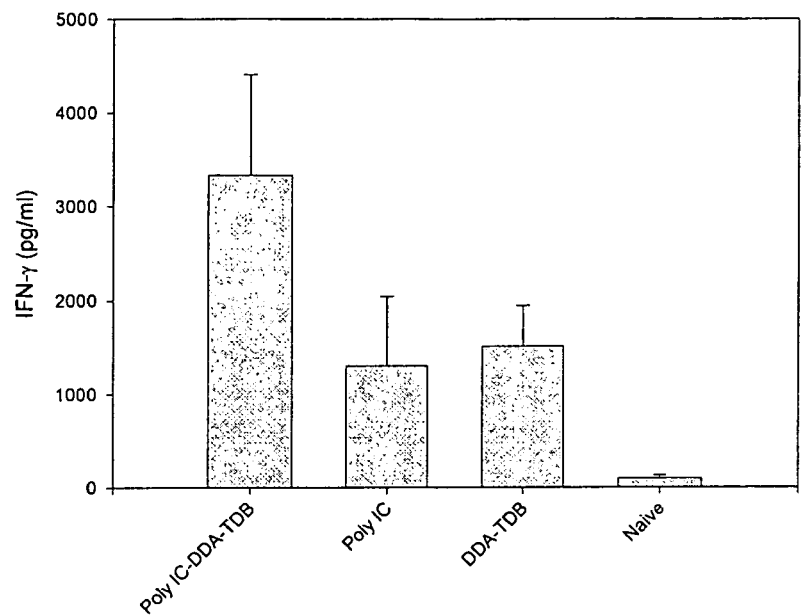

FIG. 10A is a bar chart showing the release of IFN-gamma from splenocytes isolated from BALB/C mice immunized with 2 μg of Ag85B-ESAT-6 in either 250 μg DDA/50 μg TDB, 100 μg of Poly IC, or 250 μg DDA/50 μg TDB/100 μg Poly IC. The splenocytes were isolated three weeks after the third immunization and re-stimulated in vitro with 5 μg/ml of Ag85B-ESAT-6.

Figure 10B:
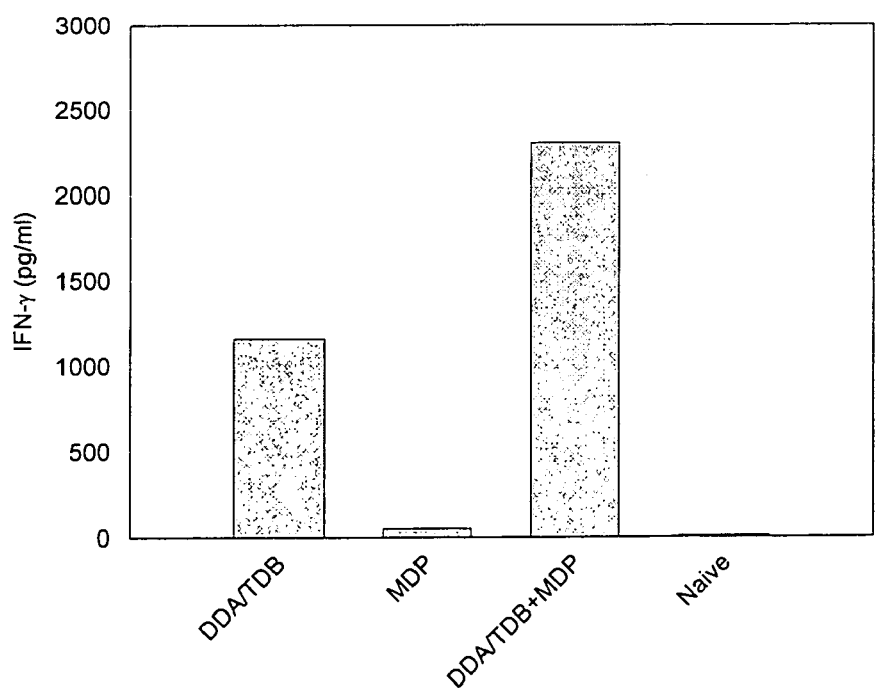

FIG. 10B is a bar chart showing the release of IFN-gamma from blood lymphocytes isolated from BALB/C mice immunized with 2 μg of Ag85B-ESAT-6 in either 250 μg DDA/50 μg TDB, 25 μg of MDP, or 250 μg DDA/50 μg TDB/25 μg MDP. The blood cells were isolated three weeks after the third immunization and re-stimulated in vitro with 5 μg/ml of Ag85B-ESAT-6.

Figure 11:
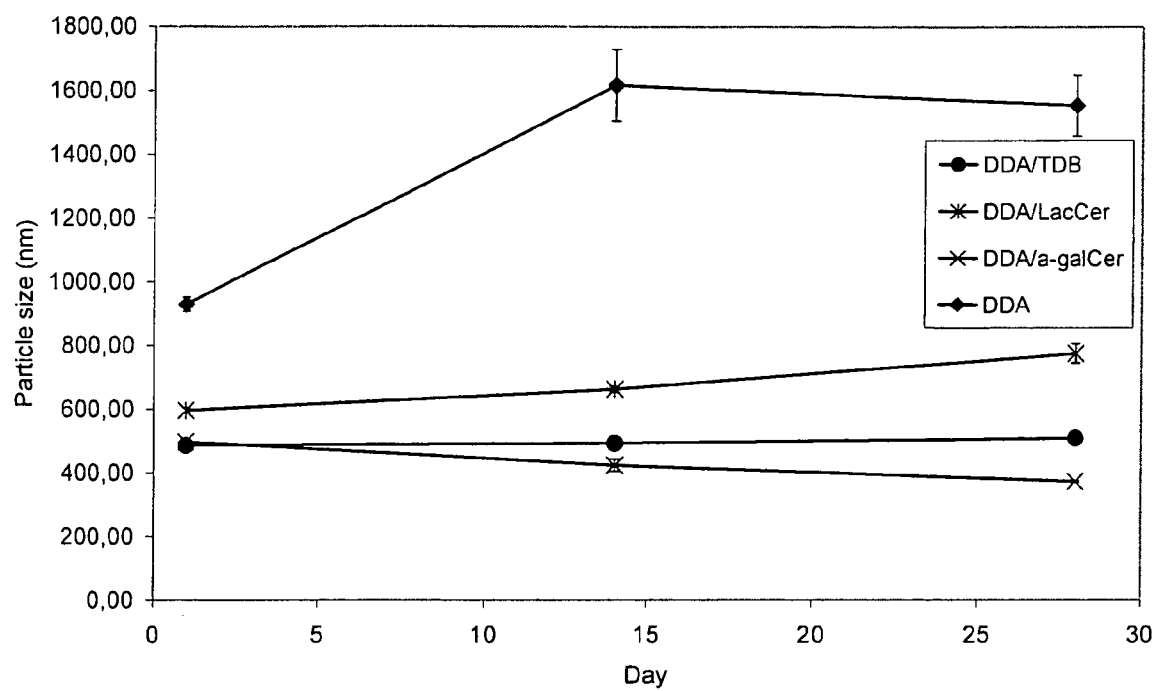

FIG. 11 is a line graph of the time development of average particle size of DDA liposomes (-♦-) and DDA liposomes containing 11 mol % TDB (-●-), 11 mol % lactocyl ceramide (-*-) and 11 mol % α-galactosyl ceramide (-X-). The liposomes were dispersed in 10 mM Tris buffer adjusted to pH 7.4. A significant increase was observed for DDA liposomes without glycolipid after 14 days. Indicating that other glycolipids than TDB can stabilize DDA.

DETAILED DESCRIPTION OF THE INVENTION

The present invention discloses a new method of stabilizing cationic liposomes in aqueous formulations with glycolipids. Cationic liposomes e.g. made from amphiphilic quaternary ammonium compounds are stabilized by incorporating glycolipids into the liposomal membranes.

A preferred embodiment of the invention is when the quaternary ammonium compound is the bromide-, chloride-, sulfate-, phosphate- or acetate-salt of dimethyldioctadecylammonium (DDA) or dimethyldioctadecenylammonium (DODA) compounds.

Other preferred quaternary ammonium compounds are 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DODAP) and N-[1-(2,3-dioleyloxy)propyl]-N,N,N-trimethylammonium (DOTMA).

The glycolipid for stabilizing the liposomes is preferably alpha,alpha'-trehalose 6,6' dibehenate (TDB) or alpha,alpha'-trehalose 6,6'-dimycolate (TDM). The mole percentage of the glycolipid in the formulation can be from 0.5 to 95 mole % but preferably 2.5 to about 20 mole % and more preferably from about 5 to about 18 mole %.

The invention also presents the use of these stabilized liposomes as an adjuvant e.g. for use in vaccine compositions. In particular the invention relates to vaccines with adjuvants in aqueous media for immunization, where the final product is stable.

The present invention also discloses a liposome product stabilized by the above described method for use as a vaccine adjuvant where the vaccine can be against any disease e.g. tuberculosis, malaria, chlamydia etc.

"Liposomes" are defined as closed vesicles structures made up of one or more lipid bilayers surrounding an aqueous core. Each lipid bilayer is composed of two lipid monolayers, each of which has a hydrophobic "tail" region and a hydrophilic "head" region. In the bilayer, the hydrophobic "tails" of the lipid monolayers orient toward the inside of the bilayer, while the hydrophilic "heads" orient toward the outside of the bilayer. Liposomes can have a variety of physicochemical properties such as size, lipid composition, surface charge, fluidity and number of bilayer membranes. According to the number of lipid bilayers liposomes can be categorized as unilamellar vesicles (UV) comprising a single lipid bilayer or multilamellar vesicles (MLV) comprising two or more concentric bilayers each separated from the next by a layer of water. Water soluble compounds are entrapped within the aqueous phases/core of the liposomes opposed to lipophilic compounds which are trapped in the core of the lipid bilayer membranes.

"Micelles" are defined as a colloidal aggregate of amphiphilic molecules, which occurs at a well-defined concentration known as the critical micelle concentration (CMC). The typical number of aggregated molecules in a micelle (aggregation number) is 50 to 100. Micelles can be spherical comprised of surfactant molecules oriented so that the hydrocarbon tails are oriented toward the center and the polar head portions are oriented toward the external aqueous environment. Other possible structures include inverted micelles and cylindrical micelles.

The term "cationic lipid" is intended to include any amphiphilic lipid, including synthetic lipids and lipid analogs, having hydrophobic and polar head group moieties, a net positive charge at physiological pH, and which by itself can form spontaneously into bilayer vesicles or micelles in water.

One particular preferred type of cationic lipids used in this invention is quaternary ammonium compounds having the general formula $NR^1R^2R^3R^4$—X wherein $R^1$ and $R^2$ independently each is a short chain alkyl group containing from 1 to 3 carbon atoms, $R^3$ is independently hydrogen or a methyl or an alkyl group containing from 12 to 20 carbon atoms, preferably 14 to 18 carbon atoms, and $R^4$ is independently a hydrocarbon group containing from 12 to 20 carbon atoms, preferably from 14 to 18 carbon atoms. X is a pharmaceutical acceptable anion, which itself is nontoxic. Examples of such anions are halide anions, chloride, bromide and iodine. Inorganic anions such as sulfate and phosphate or organic anions derived from simple organic acids such as acetic acid may also be used. The $R^1$ and $R^2$ groups can be methyl, ethyl, propyl and isopropyl, whereas $R^3$ can be hydrogen, methyl or dodecyl, tridecyl, tetradecyl, pentadecyl, hexadecyl, heptadecyl, octadecyl nonadecyl and eicocyl groups and $R^4$ can be dodecyl, tridecyl, tetradecyl, pentadecyl, hexadecyl, heptadecyl, octadecyl nonadecyl and eicocyl groups. However, also other $C_{12}$-$C_{20}$ hydrocarbon groups are possible because even though the $R^3$ and $R^4$ groups preferably are saturated with no branched side chains they may in minor degree be branched having e.g. methyl and ethyl side chains. $R^3$ and $R^4$ may also have a minor degree of unsaturation, e.g. containing 1-3 double bonds each, but preferably they are saturated alkyl groups. The cationic lipid is most preferably dimethyldioctadecylammonium bromide or chloride (DDA-B or DDA-C) or the sulfate, phosphate or acetate salt hereof (DDA-X), or dimethyldioctadecenylammonium bromide or chloride (DODA-B or DODA-C) or the sulfate, phosphate or acetate compound hereof (DODA-X). Other types of preferred cationic lipids used in this invention include but are not limited to 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DODAP) and N-[1-(2,3-dioleyloxy) propyl]-N,N,N-trimethylammonium (DOTMA).

The cationic liposomes are stabilized by incorporating glycolipids into the liposome membranes. By incorporating is meant procedures to imbed a molecule's hydrophobic region and hydrophylic region in a corresponding hydrophobic and hydrophilic region or moiety of a membrane, micelle, liposome or bilayer. Procedures for incorporating glycolipids in liposomes can be "the thin film method", "the reverse-phase evaporation method" and "the organic solution injection method" and future—at the present time unknown methods having the same effect of incorporating glycolipids into the liposome membranes. All the present known methods are mentioned in the background of invention chapter. The most preferred method for this invention is the thin film method.

A glycolipid is defined as any compound containing one or more monosaccharide residues bound by a glycosidic linkage to a hydrophobic moiety such as a long chain fatty acid, acylglycerol, a sphingoid, a ceramide or a prenyl phosphate. The glycolipids of this invention can be of synthetic, plant or microbial origin e.g. from mycobacteria.

One class of glycolipids used in this invention is acylated (or alkylated) glycosides, which consists of one or two sugars residues esterified to one, two or even three fatty acids. The fatty acids can be either straight chain including saturated fatty acids e.g. myristic acid C14:0, pentadecanoic acid C:15, palmitic acid C16:0, heptadecanoic acid C17:0, steric acid C18:0, nonadecanoic acid C:19, arachidic acid, C:20, henecosanoic C21:0, behenic acid C:22 and unsaturated fatty acids e.g. oleic acid C18:1n-9 linoleic acid 18:2n-6, or complex branched fatty acids such as mycolic acid, methoxymycolic acids, ketomycolic acids, epoxymycolic acids and corynomycolic acid. The sugar residues can be either simple monosaccharides e.g. glucose and fructose or disaccharides comprising two covalently linked monosaccharides e.g. sucrose consisting of glucose and fructose and trehalose in which two glucose units are joined by a glycosidic linkage. One type of glycolipids used in this invention is cell wall glycolipids isolated from mycobacterium, which consists of a disaccharide esterified to one, two, or three either normal palmitic acid, C16:0; oleic acid, C18:1n-9; linoleic acid, 18:2n-6 or complex hydroxy, branched-chain fatty acids i.e. mycolic acid residues ranging in length from 60 to 90 carbon atoms. Other bacterial glycolipids used in this invention have shorter fatty acid chains e.g. corynomycolic (22-36 carbons) or nocardomycolic (44-60 carbons) acids isolated from *Corynobacterium, Nocardia*. A preferred mycobacterial glycolipid is alpha,alpha'-trehalose 6,6'-dimycolate (TDM) often referred to as cord factor, which is one of the most important immunomodulatory components of the mycobacterial cell wall. In a particular preferred embodiment the glycolipid consist of the disaccharide alpha,alpha'-trehalose esterified to two docosanoic fatty acids (behenic acid) e.g. alpha,alpha'-trehalose 6,6'-dibehenate (TDB), which is a pure synthetic analog to TDM.

Other classes of glycolipids used in this invention include but are not limited to:

Glycolipids based on glycerol: These lipids consist of a mono- or oligosaccharide moiety linked glycosidically to the hydroxyl group of glycerol which may be acylated (or alkylated) with one or two fatty acids. Furthermore, these glycolipids may be uncharged and, therefore often called neutral glycoglycerolipids, or may contain a sulfate or a phosphate group.

Glycolipids based on ceramides: Glycosphingolipids have according to the structure of the carbohydrate moiety been divided into neutral glycosphingolipids containing an unsubstituted glycosyl group and acidic glycosphingolipids containing a glycosyl group with an acidic carboxyl, sulphate, or phosphate group.

Lipopolysaccharides (LPS): These complex compounds are the endotoxic antigens found in the cell walls of Gram-negative bacteria (S-lipopolysaccharides). The lipid part (Lipid A) forms a complex with a polysaccharide through a glycosidic linkage. Lipid A consists of a backbone of b-1,6-glucosaminyl-glucosamine with two phosphoester groups in the 1-position of glucosamine I and in the 4-position of glucosamine II. The 3-position of glucosamine II forms the acid-labile glycosidic linkage to the long-chain polysaccharide. The other groups are substituted (in *Escherichia*) with hydroxylated fatty acids as hydroxymyristate (two ester-linked and two amide-linked) and normal fatty acids (laurate). A particular preferred lipopolysaccharide of this invention is monophosphoryl derivatives of lipid A (MPL), which are non toxic and have excellent adjuvant properties.

Glycosides of sterols: This family consists of one carbohydrate unit linked to the hydroxyl group of one sterol molecule. The sterol moiety was determined to be composed of various sterols: cholesterol, campesterol, stigmasterol, sitosterol, brassicasterol and dihydrositosterol. The sugar moiety is composed of glucose, xylose and even arabinose.

Glycosides of fatty acids or alcohols: A great number of simple glycolipids are found in bacteria, yeasts and in lower organisms (sponges). These compounds are composed of a glycosyl moiety (one or several units) linked to one hydroxyl group of a fatty alcohol or a hydroxy fatty acid or to one carboxyl group of a fatty acid (ester linkage). These compounds frequently possess interesting physical or biological properties. Some of them are industrially produced for their detergent properties (alkyl glycosides).

An Alkyl chain refers to an aliphatic hydrocarbon chain which may be straight or branched. The chain can be saturated or it may contain one or more double bounds e.g. being unsaturated.

An acyl chain refers to an alkyl-OC(O) group, wherein the alkyl group is as previously described.

Fatty acid chain refers to a branched or unbranched saturated or unsaturated hydrocarbon chain of alkyl or acyl groups.

The term pharmaceutically acceptable refer to a substance which does not interfere with the effectiveness or the biological activity of the active ingredients and which is not toxic to the host or the patient.

Phase transition temperature or $T_m$ is the temperature at which the liposomal bilayer goes from a lower temperature gel-phase, characterized by ordered fatty acid chains (a solid-ordered phase) to a high-temperature fluid-phase in which the fatty acid chains have a high degree of conformational disorder (a liquid-disordered phase), as measured by differential scanning calorimetry (DSC).

By stability of a pharmaceutical formulation is meant the capacity of the formulation to remain within defined limits during the shelf life of the product. Liposomal dispersions exhibit chemical as well as physical stability characteristics.

Chemical stability is related to chemical degradation whereas physical stability relates to the colloidal stability of the system.

The physical stability of liposomal dispersions is determined by the inter-vesicular interactions, which depends on the balance between attractive and repulsive forces. Colloidal systems are stabilized by repulsive forces i.e. electrostatic repulsion and steric repulsion due to differences in chemical potential between water in the bulk and in the interaction region.

An adjuvant is defined as a substance that non-specifically enhances the immune response to an antigen. Depending on the nature of the adjuvant it can promote a cell-mediated immune response, a humoral immune response or a mixture of the two. Since the enhancement of the immune response is non-specific, it is well understood in the field that the same adjuvant can be used with different antigens to promote responses against different targets e.g. with an antigen from *M. tuberculosis* to promote immunity against *M. tuberculosis* or with an antigen derived from a tumor, to promote immunity against tumors of that specific kind.

Quaternary ammonium compounds for example dimethyldioctadecylammonium bromide, -chloride or other organic or inorganic salts hereof (DDA-B, DDA-C or DDA-X), dimethyldioctadecenylammonium chloride, -bromide or other organic or inorganic salts hereof (DODA-C, DODA-B or DODA-X), or 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DODAP) and N-[1-(2,3-dioleyloxy)propyl]-N,N,N-trimethylammonium (DOTMA) has the ability to form lipid aggregates such as lipid bilayers, liposomes of all types both unilamellar and multilamellar, micelles and the like when dispersed in an aqueous medium. The lipid membranes of these structures provide an excellent matrix for the inclusion of other amphiphilic compounds such as glycolipids which are shown to stabilize vesicle dispersions of this invention.

Moreover, glycolipids e.g. TDB and TDM have immunostimulatory properties themselves and can act in a synergistic way with the quaternary ammonium compounds to enhance the immune response. Furthermore, macromolecules e.g. oligonucleotide, peptide or protein antigens can be entrapped within the aqueous phase of both unilamellar and multilamellar liposomes.

The hydrophobic acyl chains of, for example, TDB is expected to be embedded in the hydrophobic region of the lipid bilayers made from quaternary ammonium compounds of this invention, thus immobilizing the hydrophilic trehalose head-groups at the interface between the hydrophobic region and the bulk water. The strongly hydrated sugar head-groups increase the overall hydration of the interface leading to a potential increase in hydration forces which prevents close contact of opposing bilayers that are required for aggregation or fusion of vesicles. Furthermore as a consequence of the hydration of the interface the fluidity of the bilayer might increase which also tends to stabilize the vesicles.

The dispersion media used in the formulations of this invention may be any suitable aqueous solvent. However, the stability of the liposomal formulations appears to be sensitive to anions, like phosphate and sulphate ions. Thus, it is preferred that the adjuvant compositions of the inventions are formed in the absence or low levels of such ions.

When used as a vaccine adjuvant an antigenic component is added to the adjuvant solution possibly together with other immunomodulators such as MPL (monophosphoryl lipid A) or derivatives thereof, polyinosinic polycytidylic acid (poly-IC), muramyl dipeptide (MDP) or analogs thereof, zymosan, double-stranded RNA (dsRNA), DC-Chol, CpG oligodeoxynucleotides, and tamoxifen. An antigenic component or substance is a molecule, which reacts with preformed antibody and/or the specific receptors on T and B cells. In the context of vaccination, a molecule that can stimulate the development of specific T or B cells, leading to the formation of a memory population of immune cells that will promote a faster "memory" response if the antigen is encountered a second time by immune cells. Since memory populations are rarely clonal, in practice this means that an antigen is any molecule or collection of molecules, which can stimulate an increase in immune responses when it is re-encountered by immune cells from an individual who has previously been exposed to it.

The antigenic component or substance can be a polypeptide or a part of the polypeptide, which elicits an immune response in an animal or a human being, and/or in a biological sample determined by any of the biological assays described herein. The immunogenic portion of a polypeptide may be a T-cell epitope or a B-cell epitope. In order to identify relevant T-cell epitopes which are recognized during an immune response, it is possible to use a "brute force" method: Since T-cell epitopes are linear, deletion mutants of the polypeptide will, if constructed systematically, re-veal what regions of the polypeptide are essential in immune recognition, e.g. by subjecting these deletion mutants e.g. to the IFN-gamma assay described herein. Another method utilizes overlapping oligopeptides (preferably synthetic having a length of e.g. 20 amino acid residues) derived from the polypeptide. These peptides can be tested in biological assays (e.g. the IFN-gamma assay as described herein) and some of these will give a positive response (and thereby be immunogenic) as evidence for the presence of a T cell epitope in the peptide. Linear B-cell epitopes can be determined by analyzing the B cell recognition to overlapping peptides covering the polypeptide of interest as e.g. described in Harboe et al, 1998.

Although the minimum length of a T-cell epitope has been shown to be at least 6 amino acids, it is normal that such epitopes are constituted of longer stretches of amino acids. Hence, it is preferred that the polypeptide fragment of the invention has a length of at least 7 amino acid residues, such as at least 8, at least 9, at least 10, at least 12, at least 14, at least 16, at least 18, at least 20, at least 22, at least 24, and at least 30 amino acid residues. Hence, in important embodiments of the inventive method, it is preferred that the polypeptide fragment has a length of at most 50 amino acid residues, such as at most 40, 35, 30, 25, and 20 amino acid residues. It is expected that the peptides having a length of between 10 and 20 amino acid residues will prove to be most efficient as diagnostic tools, and therefore especially preferred lengths of the polypeptide fragment used in the inventive method are 18, such as 15, 14, 13, 12 and even 11 amino acids.

A vaccine is defined as a suspension of dead, attenuated, or otherwise modified microorganisms (bacteria, viruses, or rickettsiae) or parts thereof for inoculation to produce immunity to a disease. The vaccine can be administered either prophylactic to prevent disease or as a therapeutic vaccine to combat already existing diseases such as cancer or latent infectious diseases but also in connection with allergy and autoimmune diseases. The vaccine can be emulsified in a suitable adjuvant for potentiating the immune response.

The vaccines are administered in a manner compatible with the dosage formulation, and in such amount as will be therapeutically effective and immunogenic. The quantity to be administered depends on the subject to be treated, including, e.g., the capacity of the individual's immune system to mount an immune response, and the degree of protection desired. Suitable dosage ranges are of the order of several hundred micrograms active ingredient per vaccination with a preferred range from about 0.1 µg to 1000 µg, such as in the range from about 1 µg to 300 µg, and especially in the range from about 10 µg to 50 µg. Suitable regimens for initial administration and booster shots are also variable but are typified by an initial administration followed by subsequent inoculations or other administrations.

The manner of application may be varied widely. Any of the conventional methods for administration of a vaccine are applicable. These are believed to include oral or mucosal application on a solid physiologically acceptable base or in a physiologically acceptable dispersion, parenterally, by injection or the like. The dosage of the vaccine will depend on the route of administration and will vary according to the age of the person to be vaccinated and, to a lesser degree, the size of the person to be vaccinated.

The vaccines are conventionally administered parenterally, by injection, for example, either subcutaneously or intramuscularly. Additional formulations which are suitable for other modes of administration include suppositories and, in some cases, oral or mucosal formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

The vaccine of choice can e.g. be:

Protein Vaccine: A vaccine composition comprising a polypeptide (or at least one immunogenic portion thereof) or fusion polypeptide.

Live recombinant vaccines: Expression of the relevant antigen in a vaccine in a non-pathogenic microorganism or virus. Well-known examples of such microorganisms are *Mycobacterium bovis* BCG, *Salmonella* and *Pseudomonas* and examples of viruses are Vaccinia Virus and Adenovirus.

For all of these vaccine constructs, the addition of a suitable adjuvant has resulted in enhanced vaccine efficacies (Brandt et al., 2000; van Rooij et al., 2001; Wang et al., 2002; Eriksson, 2003).

Still another embodiment of the invention is a delivery system comprising the adjuvant. Liposomes have been used as delivery systems in pharmacology and medicine such as immunoadjuvants, treatment of infectious diseases and inflammations, cancer therapy, and gene therapy (Gregoriadis, 1995). Factors which may have an influence on the adjuvant effect of the liposomes are liposomal size, lipid composition, and surface charge. Furthermore, antigen location (e.g., whether it is adsorbed or covalently coupled to the liposome surface or encapsulated in liposomal aqueous compartments) may also be important. Dendritic cells can be used as antigen delivery vehicles. Loading of antigen to antigen-presenting cells, such as dendritic cells, have shown to be an effective method for generating active T-cells with a role in antitumor immunity.

The liposomes of this invention can be made by a variety of methods well known in the art.

Preferably the cationic lipid is a quaternary ammonium compound having a dimethylammonium head-group and two long hydrophobic alkyl chains comprising 12 to 20 C-atoms e.g. dimethyldioctadecylammonium bromide (DDA-B), dimethyldioctadecenylammonium chloride (DODA-C). Other types of preferred cationic lipids include but are not limited to 1,2-dioleoyl-3-trimethylammonium propane (DOTAP), 1,2-dimyristoyl-3-trimethylammonium-propane, 1,2-dipalmitoyl-3-trimethylammonium-propane, 1,2-distearoyl-3-trimethylammonium-propane and dioleoyl-3-dimethylammonium propane (DODAP) and even N-[1-(2,3-dioleyloxy)propyl]-N,N,N-trimethylammonium (DOTMA).

The glycolipid is preferably an acylated glycoside formed by one up to three fatty acids acylating one or two sugar residues. The fatty acids are either saturated or unsaturated straight chain or complex branched fatty acids. The sugar can be either simple monosaccharides or disaccharides comprising two covalently linked monosaccharides. In a particular preferred embodiment the glycolipids consists of trehalose with one or two glycoside linked fatty acid chains comprising 14 to 90 C-atoms e.g. alpha,alpha'-Trehalose 6,6' dibehenate (TDB) and alpha,alpha'-trehalose 6,6-dimycolate (TDM).

In one embodiment, liposomes of the present invention comprise a bilayer forming cationic lipid, preferably, having a quaternary ammonium head-group and two long hydrophobic alkyl chains. In a particular preferred embodiment the head-group are dimethylammonium and the hydrophobic chains are hexadecyl, octadecy or octadecenyl chains. The cationic lipids of the invention can by used alone or in any combination. Moreover, the cationic lipids or mixtures thereof can be used in combination with any neutral phospholipids such as phosphaditylcholine (PC) and phosphatidylglycerol (PG) or any other bilayer forming natural or synthetic electrostatically neutral lipids.

The cationic liposomes are stabilized by incorporating glycolipids into the liposome membranes using a film method. In contrast, this stabilizing effect will not be obtained by mixing preformed solutions of DDA and TDB which is the formulations previously described (Woodard et al, 1980, Dzata et al, 1991, Holten-Andersen et al, 2004). The glycolipid must be stably incorporated into the lipid bilayers with its hydrophobic moiety embedded in the hydrophobic region of the bilayer membrane, and its polar head group moiety oriented toward the hydrophilic surface of the membranes. The molar ratios of glycolipid added to the cationic liposomes depend on the properties of glycolipid as well as on potential excipients used in the formulation. The mole percentage of a particular glycolipid can be from 0.5 to about 95 mole %, preferably from about 2.5 to about 20 mole % and more preferably from about 5 to about 18 mole %.

In a particular preferred embodiment of the invention, the quaternary ammonium compound/cationic lipid are DDA-B and the glycolipid is TDB. Liposomes are prepared by dissolving the weighed amounts DDA-B and TDB in a suitable organic solvent in a molar percentage of 5 mole % or 10 mole % or 15 mole % at a total lipid concentration of about 1 mM, 2 mM, 5 mM or even 10 mM. The solvent is evaporated leaving a thin lipid film on the inside of the test tube. The dry lipid film is then hydrated in a pharmaceutical acceptable buffer with no or low salt concentration. Formation of stable liposome structures appears to be sensitive to the presence of ions in particular anions such as phosphate and sulphate. Preferable an organic buffer e.g. 2-Amino-2-(hydroxymethyl)-1,3-propanediol (Trometamol or simply Tris) or 2-Bis (2-hydroxyethyl)amino-2-(hydroxymethyl)-1,3-propanediol (Bis-Tris) with pH 6.0 to 8.0 and more preferably with pH 6.5 to 7.5, prepared by dissolving the Tris or Bis-Tris base in MilliQ water and then adjusting the pH by adding HCl. The buffer is not limited to Tris or Bis-Tris but may be any pharmaceutical acceptable buffer or even pure water with no added buffer substance. The mixture is heated to a temperature above the phase transition temperature of the lipid mixture, for 20 minutes vigorously shaken every 5 minutes. The resulting adjuvant formulation consists of MLV characterized by having a significant improved physical stability over ordinary cationic liposomes.

An antigenic substance i.e. a protein or peptide is added and mixed with the adjuvant formulations. Most preferably the antigenic substance is bound to the vesicles by attractive electrostatic forces or hydrophobic interactions. In a particular preferred embodiment of this invention a final vaccine against tuberculosis is prepared by mixing an adjuvant formulation containing DDA liposomes stabilized by TDB with a solution of the fusion protein Ag85B-ESAT-6. The adjuvant is prepared according to this invention comprising 2.50 mg DDA per ml (4 mM) and 0.25 mg TDB per ml (0.25 mM) corresponding a TDB concentration of about 5 mole % in a 10 mM tris buffer with pH 7.4. About 4.5 ml of this adjuvant formulation is mixed with 0.5 ml 1.0 mg/ml Tris-buffer solution of Ag85B-ESAT-6 to achieve a concentration of 100 microgram/ml of the fusion protein in the final ready-to-use vaccine.

In another preferred embodiment the antigenic substance is encapsulated within the vesicles using the dehydration-rehydration method or alternatively the antigen is incorporated using the freeze and thaw technique.

EXAMPLES

Example 1

Preparation of DDA Vesicles Containing Increasing TDB Concentrations

The TDB containing DDA vesicles were made using the thin lipid film method. Dimethyldioctadecylammonium Bromide (DDA-B, Mw=630.97) and D-(+)-Trehalose 6,6'-dibehenate (TDB, Mw=987.5) (Avanti Polar Lipids, Alabaster, Ala.) were dissolved separately in chloroform methanol (9:1) to a concentration of 10 mg/ml. Specified volumes of each individual compound were mixed in glass test tubes. The solvent was evaporated using a gentle stream of $N_2$ and the lipid films were dried overnight under low pressure to remove trace amounts of solvent. The dried lipid films were hydrated in Tris-buffer (10 mM, pH=7.4) to the concentrations specified in Table 1, and placed on a 70° C. water bath for 20 min, the samples are vigorously shaken every 5 min.

TABLE 1

List a range of adjuvant formulation prepared in accordance with the present invention.

| Mole % TDB | Concentration | | | |
| --- | --- | --- | --- | --- |
| | DDA (mM) | TDB (mM) | DDA (mg/ml) | TDB (mg/ml) |
| 0 | 10 | 0.0 | 6.25 | 0.0 |
| 0.5 | 10 | 0.05 | 6.25 | 0.05 |
| 2.5 | 10 | 0.25 | 6.25 | 0.25 |
| 6 | 10 | 0.6 | 6.25 | 0.625 |
| 12.5 | 10 | 1.3 | 6.25 | 1.25 |
| 16 | 10 | 1.9 | 6.25 | 1.875 |
| 20 | 10 | 2.5 | 6.25 | 2.5 |

Example 2

TDB Increase the Long-Term Stability of DDA Formulations

Formulations of DDA-B vesicles containing increasing concentrations of TDB were stored at 4° C. and the visual appearance of the different formulations was evaluated after one day and again after two months (Table 2). After 2 months storage at 4° C., 10 mM DDA formulations (Sample 02) contained 16 mole % TDB, (Sample 03) contained 12.5 mole % TDB, (Sample 04) contained 6 mole % TDB, (Sample 05) contained 2.5 mole % TDB, (Sample 06) contained 0.5 mole % TDB, and a reference sample contained only DDA. It is clear from this illustration that the suspension containing TDB are more homogeneous and without precipitates.

The evaluation clearly demonstrates that TDB stabilize the DDA vesicles. Suspensions of DDA in aqueous buffer without TDB precipitate after one day, whereas in DDA suspensions containing more than 10 mole % TDB no participate are formed. In suspensions with as low a TDB concentration as 6% only very small amounts of precipitates are formed which can be resuspended easily by gentle shaking.

TABLE 2

Describes the 2 month stability of a range of different adjuvant formulations.

| | Time stored at 4° C. | |
| --- | --- | --- |
| Mole % TDB | 1 day | 2 months |
| 0 | Precipitates | Precipitates, not possible to re-suspend |
| 0.5 | Precipitates | Precipitates, not possible to re-suspend |
| 2.5 | No Precipitates | Precipitates, phase separation, possible to re-suspend |
| 6 | No Precipitates | Small quantity of precipitates, can easily be re-suspended |
| 11 | No Precipitates | No Precipitates |
| 16 | No Precipitates | No Precipitates |
| 20 | No Precioitates | No Precipitates |

To simulate prolonged storage the suspensions were centrifuged for 30 minutes at 3000 g. The DDA-B suspensions containing more than 2.5 mole % TDB only formed very little precipitate, which could be resuspended by shaking.

Example 3

TDB is Incorporated in the Lipid Bilayer of DDA Vesicles

Lipid bilayers formed from synthetic dialkyldimethylammonium undergoes a gel to liquid crystal main phase transition at a characteristic phase transition temperature Tm. The phase transition involves melting of the dialkyl chains in the vesicular bilayers and the organization of the chains changes from a state characterized by a high degree of conformational order to state with a higher degree of disorder. A large transition enthalpy is associated with the chain melting process. This change in enthalpy is detected as a peak in the heat capacity curve with a maximum at the transition temperature, $T_m$. The transition temperature as well as the shape of the heat capacity curve depends on the nature of the polar head-group, the counter ion, and the length of the dialkyl chains. Generally the $T_m$ value decreases with decreasing chain length and increasing asymmetry of the alkyl chains. The effect of a second dialkyl surfactant on the thermotropic phase behavior can provide useful information on the interaction between the two components.

Heat capacity curves were obtained using a VP-DSC differential scanning microcalorimeter (Calorimetry Sciences Corp., Provo) of the power compensating type with a cell volume of 0.34 mL. Three consecutive upscans of 0.34 ml sample were performed at 30 C/h. The samples were equilibrated for 50 min at the starting temperature.

The DSC thermograms of the two component system consisting of DDA-B and TDB shown in FIG. 2 demonstrate a marked influence of increasing the molar concentration of TDB on the lipid-membrane thermodynamics. The membrane insertion of TDB in the bilayers of the DDA liposomes is demonstrated by the lowering of the main phase transition temperature $T_m$. The gel to fluid transition of the pure DDA-B liposomes is characterized by a narrow well-defined heat capacity peak at 48° C. Increasing the TDB concentration results in a broadened gel to fluid phase-coexistence, where both gel and fluid phase exists at the same time.

The phase transition temperature of the DDA-B liposomes containing 20 mole % TDB is shifted downward about 5° C. below that of pure DDA-B. The insertion of TDB in the DDA-B liposome membranes have a tendency to causes the phase transition peak to split into two. This is most likely due to a small-scale compositional phase separation in the lipid membranes during the gel to fluid transition process. The thermodynamic parameters are shown in table 3.

The stabilizing effect of TDB is most likely caused by the strongly hydrated trehalose head-groups of TDB, anchored in the DDA-B liposome membrane, which prevent dehydration and fusion of the vesicular bilayers.

TABLE 3

The thermodynamic parameters for the DDA-B liposomes containing increasing TDB concentrations obtained using differential scanning calorimetry (DSC) at a scan rate of 30° C./h. The liposomes were dispersed in 10 mM Tris buffer with pH 7.4 and the total lipid concentration was 5 mM.

| Mole % | Tm (° C.) | Area | $\Delta T^{1/2}$ (° C.) |
| --- | --- | --- | --- |
| 0 | 47.24 | 8932 | 0.33 |
| 1 | 46.92 | 10830 | 0.46 |
| 5 | 45.94 | 8009 | 1.79 |
| 10 | 43.18 | 11252 | 2.92 |
| 15 | 42.80 | 9793 | 1.13 |
| 20 | 43.55 | 14139 | 2.26 |

To evaluate whether the transition state was influenced by the addition of a protein antigen, liposomes composed of DDA and TDB were added in increasing concentrations of the mycobacterial fusion protein Ag85B-ESAT-6 and the formulations analyzed by differential scanning calorimetry. As depicted in FIG. 3, the phase transition temperature do not change by the incorporation of a protein.

Example 4

Particle Size of DDA Liposomes Containing TDB

Example 4A

The Stability of DDA-B is Enhanced by Incorporation of TDB

The stability of particles of DDA-B containing increasing concentrations of TDB and prepared by the film method, was measured by dynamic light scattering measurements using a Malvern ZetaSizer 4 (Malvern Instruments Ltd. UK). Formulations of DDA-B particles with 0, 6, 11 and 20 mol % of TDB incorporated was dispersed in 10 mM Tris buffer with pH 7.4 on day 0. Measurements were done on day 0, 14, 28, 42, 56 and 105 after preparation (FIG. 4). Comparison of the particle size stability over time shows that incorporation of TDB stabilizes the DDA-B particles and prevents them from aggregating. In contrast, the formulation with DDA alone aggregated after a few days storage at 4° C. and after day 42 no further particle size measurements were possible due to aggregation. These data supports the visual impression of the DDA and DDA/TDB formulations, described in Example 2.

Example 4B

The Stability of the DDA-B Particles is Efficiently Enhanced by Incorporation of TDB Instead of Mixing the Two Components by the Aqueous Heat Method or by Adding the Sugar Part Being Trehalose The necessity of incorporation of TDB into the DDA-B particles for them to be stable was investigated by dynamic light scattering measurements using a Malvern ZetaSizer 4 (Malvern Instruments Ltd. UK). The particle size of DDA-B particles containing 11 mol % TDB prepared by the film method was compared with DDA-B particles mixed with 11 mol % TDB (the aqueous heat method previously described by Holten-Andersen). Both formulations were dispersed in 10 mM Tris buffer with pH 7.4. Measurements were done on day 0, 14 and 28 after preparation (FIG. 5). Comparison of the particle size stability over time shows that incorporation of TDB stabilizes the DDA-B particles compared to mixing the two components prevents them from aggregating To investigate whether the lipid part of TDB is necessary to stabilize the DDA-B particles, the particle size of DDA-B particles containing 11 mol % TDB prepared by the film method was compared with DDA-B particles containing 10% (w/v) sucrose and trehalose respectively. All formulations were dispersed in 10 mM Iris buffer with pH 7.4. Measurements were done on day 0, 14 and 28 after preparation (FIG. 6). Comparison of the particle size stability over time shows that the lipid part of TDB is essential for the stabilization of the DDA-B liposomes. 1 DB but not trehalose and sucrose prevent DDA-TDB liposomes from aggregating. (Severe aggregation was observed in 10 mM DDA formulations containing 10% (w/v) trehalose after 14 days of storage at 4° C.)

Example 5

Antigen is Adsorbed to the TDB Containing DDA Vesicles

SDS-PAGE analysis of supernatant and resuspended pellet of ultracentrifuged Ag85B-ESAT-6 of final ready-to-use vaccines was performed to visualize antigen adsorption to the cationic liposomes. The adjuvant comprised cationic liposomes composed of DDA stabilized by incorporation of 15 mole % of the glycolipid 1 DB. The Ag85B-ESAT-6 (Mw 45 KDa) concentration in the final vaccine was 40, 80, 160, and 200 microgram/ml and the DDA and TDB concentrations were 10 and 0.6 mM, respectively. The vaccines were ultracentrifuged (100,000 g) for 30 mm and SDS-PAGE analysis was performed on the supernatant and on the pellet resuspended in the original volume of Tris buffer (FIG. 7). A reference sample containing 50 microgram Ag85B-ESAT-6 per ml was loaded in lane 1 and a molecular weight marker was loaded in lane 2. Protein bands were visualized by coomassie staining. No visible bands were observed in the lanes loaded with the supernatants, whereas clear bands at an approximate molecular weight at 45 kDa was observed in the lanes loaded with the resuspended pellets, indicating that all or almost all the antigen is adsorbed to the cationic liposomes.

Example 6

DDA Combined with TDB Promotes an Efficient Immune Response to Ag85B-ESAT-6

It is a general accepted that adjuvants have some selectivity for the induction of a certain class of immune response. Since the importance of a Th1 cytokine release based on IFN-γ production has been shown to be essential in the resistance to TB (Flynn et al., 1993; Cooper et al., 1993), DDA-B liposomes containing 20 mole % TDB was prepared as described in example 1 of this invention and mixed with a Tris buffer solution of Ag85B-ESAT-6 to a final vaccine. The concentration in the final vaccine was 250 μg of DDA, 100 μg TDB and 2 μg Ag85B-ESAT-6. For comparison, another vaccine was included, which was composed of the same amounts of DDA and TDB, but prepared as previously described in DMSO (Holten-Andersen et al, 2004), i.e. without incorporating TDB in the liposomes by the film method. Mice were immunized three times and one week after the $3^{rd}$ vaccination the specific immune responses of blood cells were investigated (FIG. 8). A much higher response was observed after immunising with DDA/TDB prepared by the film method compared to the previously described method, demonstrating that preparation of DDA/TDB by the film method enhances the adjuvant effect compared to that of a simple mixing of DDA/TDB.

Similarly, the immune response of DDA/TDB prepared by the film method was compared to that of an aluminium-based adjuvant, Alhydrogel, already approved for clinical use. As shown in FIG. 9, immunization with DDA/TDB leads to high level of IFN-γ and low levels of IL-5 whereas Alhydrogel-immunized mice exhibited an opposite pattern with neglible IFN-γ secretion and higher levels of IL-5.

The ability of DDA/TDB to generate a humoral response was investigated by monitoring the Ag85B-ESAT-6 specific IgG antibody response five weeks after the first immunization. The concentration in the final vaccine was 250 μg of DDA, 100 μg TDB and 2 μg Ag85B-ESAT-6. A group of mice received Ag85B-ESAT-6 in Alhydrogel for comparison. As shown in table 5, high titers of specific IgG were present in sera from mice vaccinated with Ag85B-ESAT-6 in DDA/TDB. Compared with titers obtained after immunization with Ag85B-ESAT-6/Alhydrogel, the adjuvant formulation comprising DDA/TDB induced higher level of specific antibodies.

TABLE 5

Antigen-specific antibody midpoint titers in serum from Ag85B-ESAT-6 immunized mice

| | Total IgG[a] |
|---|---|
| Naïve control | <100 |
| Ag85B-ESAT-6/Alhydrogel | 51600 |
| Ag85B-ESAT-6/DDA/TDB | 218000 |

[a]Ag85B-ESAT-6 specific IgG levels 5 weeks after the first immunization as measured by ELISA.

Example 6A

Enhancement of Immune Responses by Incorporating a Third Component in the DDA/TDB Combination Recently, ligands for Toll-like receptors (TLR) have been considered attractive targets for inclusion in novel adjuvant formulations. In order to investigate the effect of incorporating other immunostimulatory components i.e. TLR-ligands in the DDA/TDB formulation, mice were immunized with 2 μg Ag85B-ESAT-6 in 250 μg DDA/50 μg TDB and selected immunomodulators. These included 100 μg of Poly IC (Polyinosinic-polycytidylic acid, Sigma Aldrich) added to the preformed DDA-TDB liposomes known to be a ligand for TLR3 as well as 25 µg of muramyldipeptide (MDP) conferring TLR2/TLR4 activation. MDP was included in the DDA-TDB lipid film before hydration.

Three weeks after the last immunization, splenocytes or blood cells (as indicated in the figure legend) were purified from individual mice and the level of IFN-γ release measured after restimulation in vitro with 5 µg/ml of Ag85B-ESAT-6. Compared to the immune response generated with either DDA/TDB alone or the third components (Poly IC and TDM) alone, the formulations encompassing all three components gave rise to an enhanced immune response showing the synergy between DDA/TDB and the immunomodulators (FIGS. 10A and B).

Example 7

The Stability of the DDA-B Particles is Efficiently Enhanced by Incorporation of Other Glycolipids than TDB To exemplify that DDA-B particles can be stabilized by other glycolipids than TDB, 11 mol % β-D-Lactosyl Ceramide (β-LacCer), 11 mol % β-Galactosyl Ceramide (β-GalCer) and 44 w/w % G(M1) gangliosides respectively. The formulations was prepared by the film method and dispersed in 10 mM Tris buffer with pH 7.4 on day 0.

Particle size was measured by dynamic light scattering measurements using a Malvern Zeta-Sizer 4 (Malvern Instruments Ltd. UK). Measurements were done on day 0, 14, 28 after preparation (FIG. 11). Comparison of the particle size stability over time shows that incorporation of glycolipids stabilizes DDA.

REFERENCES

Andersen, P. 1994. Effective vaccination of mice against *Mycobacterium tuberculosis* infection with a soluble mixture of secreted mycobacterial proteins. Infect. and Immun. 62:2536-2544.

Bally et al., 1987. U.S. Pat. No. 4,975,282

Bangham, A. D., M. M. Standish, and J. C. Watkins. 1965. Diffusion of univalent ions across lamellae of swollen phospholipids. J. Mol. Biol. 13: 238.

Ben-Yehuda et al. 2003. Immunogenicity and safety of a novel IL-2-supplemented liposomal influenza vaccine (INFLUSOME-VAC) in nursing-home residents. Vaccine 21; 3169-3178

Brandt, L., M. Elhay, I. Rosenkrands, E. B. Lindblad, and P. Andersen. 2000. ESAT-6 subunit vaccination against *Mycobacterium tuberculosis*. Infect. Immun. 68:791-795.

Campbell et al. 2002. WO0230959

Carmona-Ribeiro, A. M., H. Chaimovich. 1986. Salt-induced aggregation and fusion of dioctadecyldimethylammonium chloride and sodium dihexadecylphosphate vesicles. Biophys J. 50(4): 621-8.

Collins, H. L., and S. H. Kaufmann. 2001. The many faces of host responses to tuberculosis. Immunology. 103:1-9.

Cooper A. M., D. K. Dalton, T. A. Stewart, J. P. Griffen, D. G. Russel, and I. M. Orme. 1993. Disseminated tuberculosis in interferon gamma gene-disrupted mice, J. Exp. Med. 178: 2243-2247

Crowe, L. M, B. J. Spargo, T. Loneda, B. L. Beaman, J. H. Crowe. 1994. Interaction of cord factor (α,α-trehalose 6,6'-dimycolate) with phospholipids. Biochim. Biophys. Acta. 1194; 53-60.

Cullis et al. 1991. U.S. Pat. No. 5,008,050

Dzata, G. K., J. H. Wyckoff, 3rd, and A. W. Confer. 1991. Immunopotentiation of cattle vaccinated with a soluble *Brucella abortus* antigen with low LPS content: an analysis of cellular and humoral immune responses. Vet Microbiol 29:15-26.

Eriksson, K., M. Frederiksson, I. Nordstrom, and J. Holmgren. 2003. Cholera toxin and its B subunit promote dendritic cell vaccination with different influences on Th1 and Th2 development. Infect. Immun. 71:1740-7.

Flynn, J. L., J. Chan, K. J. Triebold, D. K. Dalton, T. A. Stewart, and B. R. Bloom. 1993. An essential role for interferon gamma in resistance to *Mycobacterium tuberculosis* infection, J. Exp. Med. 178: 2249-2254

Gregoriadis, G. 1995. Engineering liposomes for drug delivery: progress and problems. Trends Biotechnol. 13:527-37.

Gregoriadis, G., B. Mccormack, M. Obrenovic, R. Saffie, B. Zadi, Y Perrie. 1999. Vaccine entrapment in liposomes. Methods 19 (1): 156-162.

Harboe M, A. S. Malin, H. S. Dockrell, H. G. Wiker, G. Ulvund, A. Holm, M. C. Jørgensen, P Andersen. B-cell epitopes and quantification of the ESAT-6 protein of *Mycobacterium tuberculosis* Infect. Immun. 66 (2): 717-723.

Hilgers, L. A., and H. Snippe. 1992. DDA as an immunological adjuvant. Res. Immunol. 143:494-503; discussion 574-6.

Hilgers and Weststrate. 1991. U.S. Pat. No. 5,026,546

Holland et al. 1996. WO9610392

Holten-Andersen, L., T. M. Doherty, K. V. Knudsen, and P. Andersen. 2004. DDA/TDB—a Th1-inducing adjuvant formulation for TB subunit vaccines. Infect. Immun. 72: 1608-17.

Kirby, C and G. Gregoriadis. 1984. Dehydration-rehydration vesicles—a simple method for high-yield drug entrapment in liposomes Biotechnol. 2 (11): 979-984.

Li, B., S. Li, Y. Tan, D. B. Stolz, S. C. Watkins, L. H. Block, and L. Huang. 2000. Lyophilization of cationic lipid-protamine-DNA (LPD) complexes. J Pharm Sci 89:355-64.

Lindblad, E. B., M. J. Elhay, R. Silva, R. Appelberg, and P. Andersen. 1997. Adjuvant modulation of immune response to tuberculosis sub-unit vaccines. Infection and Immunity. 65:623-629.

Olsen, A. W., L. A. H. vanPinxteren, L. M. Okkels, P. B. Rasmussen, and P. Andersen. 2001. Protection of mice with a tuberculosis subunit vaccine based on a fusion protein of antigen 85B and ESAT-6. Infect. Immun. 69:2773-2778.

Papahadjopoulos, D. and J. C. Watkins. 1967. Phospholipid model membranes. 2. permeability properties of hydrated liquid crystals. Biochim. Biophys. Acta. 135: 639.

Papahadjopoulos, D. P. 1980. U.S. Pat. No. 4,235,871

Pick U. 1981. Liposomes with a large trapping capacity prepared by freezing and thawing of sonicated phospholipid mixtures. Arch. Biochem. Biophys. 212 (1): 186-194.

Ribeiro, A. M. C. and H. Chaimovich. 1983. Preparation and characterization of large dioctadecyldimethylammonium chloride liposomes and comparison with small sonicated vesicles. Bioch. Biophys. Acta. 733: 172-179.

Spargo, B. J., L. M. Crowe, T. Ioneda, B. L Beaman, J. H. Crowe. 1991. Cord factor (α,α-trehalose 6,6'-dimycolate) inhibits fusion between phospholipid vesicles. Proc. Natl. Acad. Sci. 88: 737-740.

Stanfield, J. P., D. Gall, and P. M. Bracken. 1973. Single-dose antenatal tetanus immunisation. Lancet. 1: 215-9.

Szoka F., D. Papahadjopoulos. 1978. Procedure for preparation of liposomes with large internal aqueous space and high capture by reverse-phase evaporation. Proce. Natl. Acad. Sci. USA. 75 (9): 4194-4198.

Takahashi and Tsujii, 1985. GB2147263 van Rooij, E. M., H. L. Glansbeek, L. A. Hilgers, E. G. te Lintelo, Y. E. de Visser, W. J. Boersma, B. L. Haagmans, and A. T. Bianchi. 2002.

Protective antiviral immune responses to pseudorabies virus induced by DNA vaccination using dimethyldioctadecylammonium bromide as an adjuvant. J. Virol. 76:10540-5.

Wang, J., A. Zganiacz, and Z. Xing. 2002. Enhanced immunogenicity of BCG vaccine by using a viral-based GM-CSF transgene adjuvant formulation. Vaccine. 20:2887-98.

Woodard, L. F., N. M. Toone, and C. A. McLaughlin. 1980. Comparison of muramyl dipeptide, trehalose dimycolate, and dimethyl dioctadecyl ammonium bromide as adjuvants in *Brucella abortus* 45/20 vaccines. Infect immun 30:409-12.

Janoff et al. 1999 U.S. Pat. No. 5,922,350

The invention claimed is:

1. A method of stabilizing cationic liposomes in aqueous formulations comprising incorporating 2.5 mole % to about 20 mole % glycolipids selected from the group consisting of alpha, alpha'-trehalose 6,6' dibehenate (TDB), a ceramide and a ganglioside into the liposomes prepared from a compound selected from the group consisting of a bromide salt of dimethyldioctadeceylammonium (DDA).

2. The method of stabilizing cationic liposomes in aqueous formulations according to claim 1, comprising incorporating about 5 to about 18 mole % glycolipids into the liposomes.

3. A method of stabilizing liposomes by incorporating from 2.5 mole % to about 95 mole %, preferably from 2.5 to about 20 mole % and more preferably from about 5 to about 18 mole %, alpha,alpha'-trehalose 6,6' dibehenate (TDB) into cationic liposomes comprising an amphiphilic quaternary ammonium compound selected from the group consisting of DDA-B, DDA-C, and DOTAP.

4. The method according to claim 3, wherein the incorporating further comprises:
dissolving the quaternary ammonium compound and glycolipid in a suitable organic solvent;
evaporating the solvent to produce a lipid film;
drying the lipid film; and
hydrating the dried lipid film in a pharmaceutically acceptable buffer; and
heating the hydrated films.

5. The method according to claim 4, wherein the total lipid concentration in the organic solvent is about 1 mM to about 10 mM.

6. The method according claim 4, wherein the organic solvent is chloroform methanol.

7. The method according to claim 4, wherein the pharmaceutical acceptable buffer has no or a low salt concentration.

8. The method according to claim 4, wherein the pharmaceutical acceptable buffer is selected from 2-amino-2-(hydroxymethyl)-1,3-propanediol and 2-Bis(2-hydroxyethyl)amino-2-(hydroxymethyl)-1,3-propanediol.

9. The method according to claim 4, wherein the buffer has a pH in the range of 6.5 to 7.5.

10. A method of stabilizing liposomes in aqueous formulations comprising incorporating 2.5 mole % to about 20 mole % glycolipids into cationic liposomes comprising a quaternary ammonium compound, wherein the quaternary ammonium compound is DDA-B and the glycolipid is TDB.

11. A liposome product stabilized by the method of claim 10.

12. A liposome product according to claim 11 where an antigenic compound is encapsulated in the liposomes.

13. A liposome product according to claim 10 formulated for use in drug delivery.

14. A liposome product according to claim 12 formulated for use as an adjuvant.

15. A vaccine adjuvant comprising the liposome product according to claim 14 and an immunomodulator.

16. The vaccine adjuvant according to claim 15, wherein the immunomodulator is selected from the group consisting of monophosphoryl lipid A (MPL), derivatives of MPL, myramyl dipeptide (MDP), analogs of MDP, zymosan, double-stranded RNA (ds-RNA), cholesteryl-3 (β)N-dimethylaminoethyl (DC-Chol), CpG oligodeoxynucleotides, and tamoxifen.

17. The vaccine adjuvant according to claim 15, wherein the immunomodulator is polyinosinic polycytidylic acid.

* * * * *